US011613580B2

United States Patent
Moate et al.

(10) Patent No.: US 11,613,580 B2
(45) Date of Patent: Mar. 28, 2023

(54) ANTI-PAD4 AUTOANTIBODIES AS CLINICAL RESPONSE BIOMARKERS FOR THE TREATMENT OF RHEUMATOID ARTHRITIS

(71) Applicant: MEDIMMUNE LIMITED, Cambridge (GB)

(72) Inventors: Rachel Patricia Moate, Cambridge (GB); Alex Godwood, Cambridge (GB); Ethan Paul Grant, Gaithersburg, MD (US); Martin Michael Kari Schwickart, Gaithersburg, MD (US); Carlos Chavez, Gaithersburg, MD (US); Meina Liang, Gaithersburg, MD (US); Tomas Mikael Mustelin, Seattle, WA (US); Zhengbin Yao, Gaithersburg, MD (US); Koustubh Ranade, Gaithersburg, MD (US)

(73) Assignee: MEDIMMUNE LIMITED, Cambridge (GB)

( * ) Notice: Subject to any disclaimer, the term of this patent is extended or adjusted under 35 U.S.C. 154(b) by 195 days.

(21) Appl. No.: 16/304,055

(22) PCT Filed: May 23, 2017

(86) PCT No.: PCT/EP2017/062479
§ 371 (c)(1),
(2) Date: Nov. 21, 2018

(87) PCT Pub. No.: WO2017/202879
PCT Pub. Date: Nov. 30, 2017

(65) Prior Publication Data
US 2020/0317793 A1    Oct. 8, 2020

Related U.S. Application Data

(60) Provisional application No. 62/340,560, filed on May 24, 2016.

(51) Int. Cl.
| | |
|---|---|
| *C07K 16/28* | (2006.01) |
| *G01N 33/564* | (2006.01) |
| *A61P 19/02* | (2006.01) |
| *G01N 33/68* | (2006.01) |
| *A61K 39/00* | (2006.01) |

(52) U.S. Cl.
CPC ....... *C07K 16/2866* (2013.01); *G01N 33/564* (2013.01); *G01N 33/6854* (2013.01); *A61K 2039/505* (2013.01); *A61P 19/02* (2018.01); *C07K 2317/76* (2013.01); *G01N 2800/102* (2013.01); *G01N 2800/52* (2013.01)

(58) Field of Classification Search
CPC combination set(s) only.
See application file for complete search history.

(56) References Cited

U.S. PATENT DOCUMENTS

| | | | |
|---|---|---|---|
| 9,267,946 B2 * | 2/2016 | Auger | C07K 14/82 |
| 2013/0101611 A1 | 4/2013 | Andrade et al. | |
| 2014/0127720 A1 | 5/2014 | Rosen et al. | |

FOREIGN PATENT DOCUMENTS

| | | |
|---|---|---|
| JP | 2009156615 A | 7/2013 |
| WO | 2015/177097 A1 | 11/2015 |

OTHER PUBLICATIONS

Ishigami et al (Mod. Rheumatol. 2013, 23:794-803).*
Pollman et al (Rheumatol. Int. 2012, 32:1271-1276).*
Halvorsen et al (Ann. Rheum. Dis. 2008, 67:414-417).*
Burmester et al (Ann Rheum Dis. 2013, 72:1445-1452).*
Yu et al (Diabetes, 2012, 61:179-186).*
Zhou et al (Nature Protocols, 2014, 5:1146-1159).*
Grant et al. Lack of Autoantibodies to Peptidyl Arginine Deiminase 4 Predict Increased Efficacy of Mavrilimumab in Rheumatoid Arthritis. Arthritis Rheumatol. Published Sep. 28, 2016; 68 (suppl 10).*
Burmester et al., "Efficacy and safety of mavrilimumab in subjects with rheumatoid arthritis", Ann Rheum Dis 72:1445-1452 (2013).

* cited by examiner

*Primary Examiner* — Laura B Goddard
(74) *Attorney, Agent, or Firm* — Proskauer Rose LLP

(57) ABSTRACT

The present disclosure relates to the use of anti-PAD4 autoantibodies as a clinical biomarker for rheumatoid arthritis (RA) treatment. The disclosure further provides an assay to detect anti-PAD4 autoantibodies, assay kits for the detection of anti-PAD4 autoantibodies, as well as computer implemented diagnostic methods.

11 Claims, 1 Drawing Sheet
Specification includes a Sequence Listing.

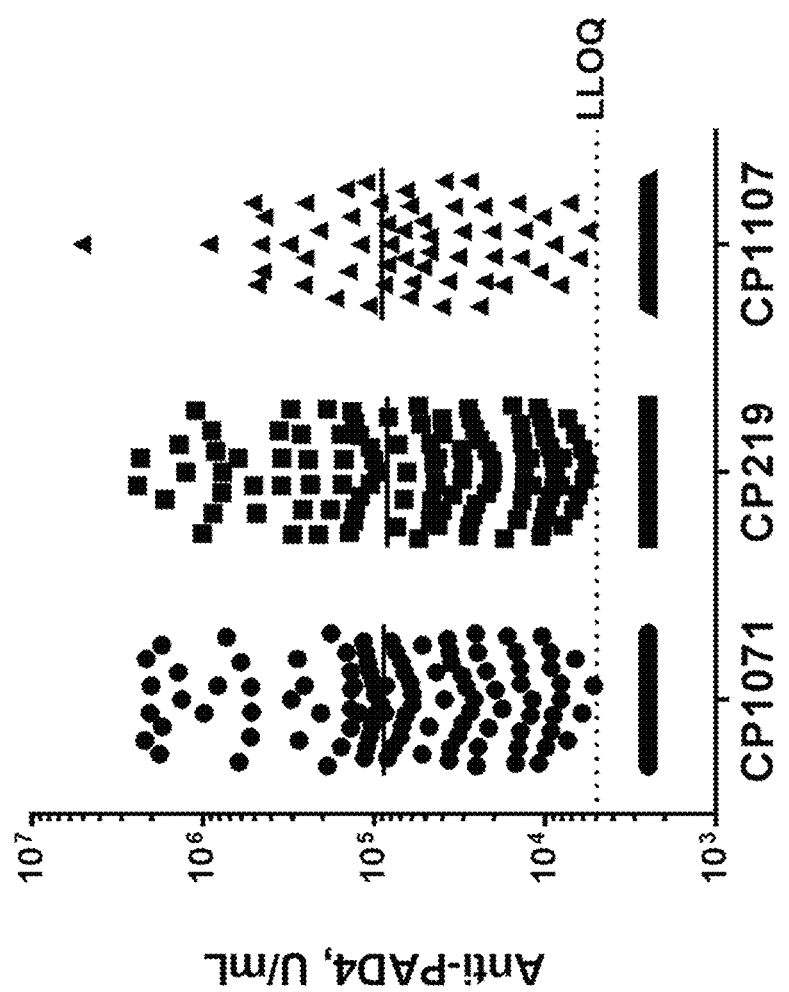

ANTI-PAD4 AUTOANTIBODIES AS CLINICAL RESPONSE BIOMARKERS FOR THE TREATMENT OF RHEUMATOID ARTHRITIS

CROSS REFERENCE TO RELATED APPLICATIONS

This application is a U.S.C. § 371 National Stage Application of International Application No. PCT/EP2017/062479, filed on May 23, 2017, which claims priority to U.S. provisional patent application Ser. No. 62/340,560, filed on May 24, 2016, the entirety of which is hereby incorporated by reference.

REFERENCE TO SEQUENCE LISTING SUBMITTED ELECTRONICALLY

The content of the electronically submitted sequence listing in ASCII text file (Name: KPL-033US_ST25.txt; Size: 19,263 bytes; and Date of Creation: Apr. 28, 2021) filed with the application is incorporated herein by reference in its entirety.

BACKGROUND

Rheumatoid arthritis (RA) is a chronic autoimmune disease affecting approximately 1% of the world's population. It is characterized by inflammation and cellular proliferation in the synovial lining of joints that can ultimately result in cartilage and bone destruction, joint deformity and loss of mobility. RA usually causes problems in several joints at the same time, often in a symmetric manner. Early RA tends to affect the smaller joints first, such as the joints in the wrists, hands, ankles and feet. As the disease progresses, joints of the shoulders, elbows, knees, hips, jaw and neck can also become involved. Unlike other arthritic conditions that only affect areas in or around joints, RA is a systemic disease which can cause inflammation in extra-articular tissues throughout the body including the skin, blood vessels, heart, lungs and muscles. Consequently, RA imposes an important economic burden on society. Considerable data also suggest that RA is associated with lowered life expectancy.

RA is a heterogeneous disease and there are no approved treatment options that are highly effective in all patients. Currently there is no cure for RA, and treatment is essentially directed towards relieving pain, reducing inflammation, and stopping or slowing joint damage and bone destruction. The current therapeutic approach is to prescribe disease-modifying antirheumatic drugs (DMARDs) early in the condition, as RA patients treated early with such drugs have better outcomes, with greater preservation of function, less work disability, and smaller risk of premature death.

RA is characterized by the presence of several types of autoantibodies. The most common forms of autoantibody present in RA patients include rheumatoid factor and anti-citrullinated protein antibodies. Based on limited publications, autoantibodies directed against peptidylarginine deiminase 4 (PAD4) are present in approximately one-third of RA patients. However, there is currently a poor understanding of the function and potential pathogenic role that anti-PAD4 autoantibodies may have in RA.

New therapeutic options, including mavrilimumab, have the potential to address the unmet medical needs of RA patients. Accordingly, a means to identify RA patients who are likely to have a positive clinical response to mavrilimumab (e.g., a diagnostic biomarker) could greatly augment the utility of this novel therapeutic. Similarly, a reliable method for detecting anti-PAD4 autoantibodies would be of great benefit for the RA population.

BRIEF SUMMARY

The present disclosure provides assays for determining the level of anti-PAD4 autoantibodies in a sample. In some embodiments, the assay for determining the level of anti-PAD4 autoantibodies comprises allowing anti-PAD4 autoantibodies present in the sample to bind to recombinant PAD4, binding ruthenylated recombinant PAD4 to the anti-PAD4 autoantibody bound to PAD4, detecting the level of anti-PAD4 autoantibodies, and determining the level of anti-PAD4 autoantibodies in the sample. In some aspects, the lower limit of quantification (LLOQ) of anti-PAD4 autoantibodies for the assay is 5000 U/mL. In some embodiments, the assays may be agglutination assays or homogeneous assays.

The present disclosure provides, inter alia, method of treating a rheumatoid arthritis (RA) patient comprising administering an antibody or antigen-binding fragment thereof that specifically binds to human granulocyte macrophage colony-stimulating factor receptor alpha (GM-CSFRα) to the patient if the level of anti-peptidylarginine deiminase 4 (anti-PAD4) autoantibodies in a sample from the patient is below the lower limit of quantification (LLOQ) for the assay. Also provided is a method of treating an RA patient comprising administering an antibody or antigen-binding fragment thereof that specifically binds to GM-CSFRα (e.g., mavrilimumab) to the patient if the level of anti-PAD4 autoantibodies in a sample from the patient is below the LLOQ for the assay, and the patient presents a level of at least one RA biomarker in a sample taken from the patient which is above or below a predetermined biomarker threshold level, or is above or below the biomarker level in one or more control samples. In some aspects, a sample is obtained from the patient. In some aspects, the sample is obtained from the patient and is submitted for measurement of the level of anti-PAD4 autoantibodies in the sample.

The present disclosure also provides a method of treating an RA patient comprising submitting a sample from the patient for measurement of the levels of anti-PAD4 autoantibodies in the sample; and administering an antibody or antigen-binding fragment thereof that specifically binds to GM-CSFRα (e.g., mavrilimumab) to the patient if the patient's level of anti-PAD4 autoantibodies in the sample is below the LLOQ for the assay. Also provided is a method of treating an RA patient comprising submitting a sample from the patient for measurement of the level of anti-PAD4 autoantibodies in the sample; and suspending the administration of an antibody or antigen-binding fragment thereof that specifically binds to GM-CSFRα (e.g., mavrilimumab) to the patient if the patient's level of anti-PAD4 autoantibodies in the sample is above the LLOQ for the assay.

The instant disclosure also provides a method of treating an RA patient comprising measuring the level of anti-PAD4 autoantibodies in a sample obtained from a patient having RA; determining whether the patient's level of anti-PAD4 autoantibodies in the sample is above or below the LLOQ for the assay; and advising a healthcare provider to administer an antibody or antigen-binding fragment thereof that specifically binds to GM-CSFRα (e.g., mavrilimumab) to the patient if the patient's level of anti-PAD4 autoantibodies is below the LLOQ for the assay. Also provided is a method of treating an RA patient comprising measuring the level of anti-PAD4 autoantibodies in a sample obtained from a patient having RA; determining whether the patient's level of anti-PAD4 autoantibodies in the sample is above or below the LLOQ for the assay; and advising a healthcare provider to suspend the administration of an antibody or antigen-binding fragment thereof that specifically binds to GM-CSFRα (e.g., mavrilimumab) to the patient if the patient's level of anti-PAD4 autoantibodies is above the LLOQ for the assay.

The present disclosure also provides a method of treating an RA patient comprising submitting a sample taken from the patient for measurement of the level of anti-PAD4 autoantibodies in the sample; and administering an antibody or antigen-binding fragment thereof that specifically binds to GM-CSFRα (e.g., mavrilimumab) to the patient if the patient's level of anti-PAD4 autoantibodies in the sample is below the LLOQ for the assay.

Also provided is a method of treating an RA patient comprising submitting a sample taken from the patient for measurement of the level of anti-PAD4 autoantibodies in the sample; and suspending the administration of an antibody or antigen-binding fragment thereof that specifically binds to GM-CSFRα (e.g., mavrilimumab) to the patient if the patient's level of anti-PAD4 autoantibodies in the sample is above the LLOQ for the assay. Also provided is method of determining whether to treat a patient diagnosed with RA with a therapeutic regimen comprising the administration of an antibody or antigen-binding fragment thereof that specifically binds to GM-CSFRα (e.g., mavrilimumab), comprising: measuring, or instructing a clinical laboratory to measure the level of anti-PAD4 autoantibodies in a sample obtained from the patient diagnosed with RA; and treating, or instructing a healthcare provider to treat the patient with a therapeutic regimen comprising the administration of an antibody or antigen-binding fragment thereof that specifically binds to GM-CSFRα (e.g., mavrilimumab) if the patient's level of anti-PAD4 autoantibodies in the sample is below the LLOQ for the assay. In some instances, the level of anti-PAD4 autoantibodies in the sample is determined using the assay of the invention.

The present disclosure also provides a method of determining whether to treat a patient diagnosed with RA with a therapeutic regimen comprising the administration of an antibody or antigen-binding fragment thereof that specifically binds to GM-CSFRα (e.g., mavrilimumab), comprising: measuring, or instructing a clinical laboratory to measure the level of anti-PAD4 autoantibodies in a sample from the patient diagnosed with RA; and suspending the treatment, or instructing a healthcare provider to suspend the treatment of the patient with a therapeutic regimen comprising the administration of an antibody or antigen-binding fragment thereof that specifically binds to GM-CSFRα (e.g., mavrilimumab) if the patient's level of anti-PAD4 autoantibodies in the sample is above the LLOQ for the assay.

Also provided is a method of selecting a patient diagnosed with RA as a candidate for treatment with an antibody or antigen-binding fragment thereof that specifically binds to GM-CSFRα (e.g., mavrilimumab) comprising: measuring, or instructing a clinical laboratory to measure the level of anti-PAD4 autoantibodies in a sample obtained from a patient diagnosed with RA; and treating, or instructing a healthcare provider to treat the patient with an antibody or antigen-binding fragment thereof that specifically binds to GM-CSFRα (e.g., mavrilimumab) if the patient's level of anti-PAD4 autoantibodies in the sample is below the LLOQ for the assay.

The present disclosure also provides a method of selecting a patient diagnosed with RA as a candidate for treatment with an antibody or antigen-binding fragment thereof that specifically binds to GM-CSFRα (e.g., mavrilimumab) comprising: measuring, or instructing a clinical laboratory to measure the level of anti-PAD4 autoantibodies in a sample obtained from a patient diagnosed with RA; and suspending, or instructing a healthcare provider to suspend the treatment of the patient with an antibody or antigen-binding fragment thereof that specifically binds to GM-CSFRα (e.g., mavrilimumab) or select an alternative treatment if the patient's level of anti-PAD4 autoantibodies in the sample is above the LLOQ for the assay.

In some aspects of the methods disclosed above, the antibody or antigen-binding fragment thereof that specifically binds to GM-CSFRα comprises mavrilimumab or an antigen-binding fragment thereof. In some aspects, the antibody or antigen-binding fragment thereof that specifically binds to GM-CSFRα consists of mavrilimumab or an antigen-binding fragment thereof. In some aspects, the antibody or antigen-binding fragment thereof that specifically binds to GM-CSFRα specifically binds to the same epitope as mavrilimumab.

In some aspects, the antibody or antigen-binding fragment thereof that specifically binds to GM-CSFRα specifically competes with mavrilimumab for binding to the same epitope. In some aspects, the antibody or antigen-binding fragment thereof that specifically binds to GM-CSFRα comprises a heavy chain variable region (VH) having the amino acid sequence set forth in SEQ ID NO: 4, and/or a light chain variable region (VL) having the amino acid sequence set forth in SEQ ID NO: 5 These are the heavy chain and light chain variable regions of mavrilimumab.

In some aspects, the antibody or antigen-binding fragment thereof that specifically binds to GM-CSFRα comprises at least one of the complementarity determining regions set forth in SEQ ID NOS: 6-11. In some aspects, the patient has been treated with one or more additional Disease-Modifying Anti-Rheumatic Drugs (DMARDs), either before, during, or after administration of an antibody or antigen-binding fragment thereof that specifically binds to GM-CSFRα. In some aspects, the DMARD is selected from abatacept, adalimumab, azathioprine, chloroquine, hydroxychloroquine, ciclosporin, D-penicillamine, etanercept, golimumab, infliximab, leflunomide, methotrexate, minocycline, rituximab, sulfasalazine, and combinations thereof. In some aspects, the sample obtained from the patient comprises one or more of whole blood, blood serum, plasma, or synovial fluid. In some aspects, the sample obtained from the patient is blood serum.

In some aspects, the methods disclosed above further comprise determining, submitting a sample from the patient for determination, or instructing a clinical laboratory to determine the expression level or activity of one or more additional biomarkers (e.g., biological biomarkers or clinical biomarkers), to determine at least one clinical status marker, or a combination thereof.

In some aspects, the antibody or antigen-binding fragment thereof that specifically binds to GM-CSFRα (e.g., mavrilimumab) is administered at a fixed dose. In some aspects, the antibody or antigen-binding fragment thereof that specifically binds to GM-CSFRα (e.g., mavrilimumab) is administered at a fixed dose of about 30 mg/dose, about 100 mg/dose, or about 150 mg/dose.

In some aspects, the patient's anti-PAD4 autoantibody level is measured in an immunoassay. In some aspects, the immunoassay employs detectably labeled PAD4. In some aspects, the detectably labeled PAD4 is ruthinylated PAD4. In some aspects, the immunoassay detects anti-PAD4-induced PAD4 crosslinking.

BRIEF DESCRIPTION OF THE DRAWINGS/FIGURES

FIG. 1 shows anti-PAD4 autoantibody levels measured in RA subjects from three different clinical studies using mavrilimumab (studies A, B, and C).

DETAILED DESCRIPTION

The present disclosure relates to using the presence or absence of anti-peptidylarginine deiminase 4 (anti-PAD4) autoantibodies in a sample from an RA patient as a biomarker to determine the appropriate course of treatment. For example, whether to administer an antibody or antigen-binding fragment thereof that specifically binds to the granulocyte macrophage colony-stimulating factor receptor alpha (GM-CSFRα). Accordingly, the disclosure provides methods for diagnosing a patient, methods for treating a patient (e.g., with an antibody such as mavrilimumab), methods for selecting or non-selecting a patient for treatment (e.g., with an antibody such as mavrilimumab), selecting a certain treatment (e.g., mavrilimumab), suspending temporarily or permanently a treatment, determining the prognosis of a patient, or monitoring the effect of a treatment, wherein those methods comprise determining the presence or absence of anti-PAD4 autoantibodies and/or quantifying the level of anti-PAD4 autoantibodies in a sample taken from the patient. In certain embodiments, the presence or absence of anti-PAD4 is determined using the assay taught here.

In order that the present disclosure can be more readily understood, certain terms are first defined. Additional definitions are set forth throughout the detailed description.

I. Definitions

In this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Wherever aspects are described herein with the language "comprising," otherwise analogous aspects described in terms of "consisting of" and/or "consisting essentially of" are also provided.

The term "about" as used in connection with a numerical value throughout the specification and the claims denotes an interval of accuracy, familiar and acceptable to a person skilled in the art. In general, such interval of accuracy is ±15%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "antibody" refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988). Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule. Thus, in view if this definition of the term "antibody," references to an antibody such as mavrilimumab refers to the mavrilimumab antibody and also to antigen-binding fragments, variants, and derivatives thereof.

By "specifically binds," it is generally meant that an antibody or fragment, variant, or derivative thereof binds to an epitope via its antigen-binding domain, and that the binding entails some complementarity between the antigen binding domain and the epitope. According to this definition, an antibody is said to "specifically bind" to an epitope when it binds to that epitope via its antigen-binding domain more readily than it would bind to a random, unrelated epitope.

An antibody or antigen-binding fragment, variant, or derivative thereof is said to competitively inhibit binding of a reference antibody or antigen-binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen-binding fragment to a given epitope by at least 90%, at least 80%, at least 70%, at least 60%, or at least 50%.

Antibodies or antigen-binding fragments, variants, or derivatives thereof disclosed herein can be described or specified in terms of the epitope(s) or portion(s) of an antigen, e.g., a target polysaccharide that they recognize or specifically bind. For example, the portion of GM-CSFR that specifically interacts with the antigen-binding domain of an anti-GM-CSFR antibody (e.g., mavrilimumab) is an "epitope."

The term "autoantibody", as used herein (e.g., to refer to an anti-PAD4 autoantibody) refers to an antibody that is produced by the immune system of a subject and that is directed against an autoantigen. Autoantibodies may attack the body's own cells, tissues, and/or organs, causing inflammation and damage. As used herein, the term "autoantigen" refers to an endogenous antigen (e.g., PAD4), or an active fragment thereof, that stimulates the production of autoantibodies in a subject's body, as in autoimmune reactions. The term also encompasses any substances that can form an antigen-antibody complex with autoantibodies present in a subject or in a biological sample obtained from a subject.

The term "treatment" is used herein to characterize a method that is aimed at delaying or preventing the onset of a disease or condition (e.g., RA); slowing down or stopping the progression, aggravating, or deteriorations of the symptoms of the condition; bringing about ameliorations or the symptoms of the condition; and/or curing the condition. A treatment may be administered prior to the onset of the disease, for a prophylactic or preventive action. It may also be administered after initiation of the disease, for a therapeutic action.

The terms "subject" or "patient" as used herein refer to any subject, particularly a mammalian subject, for whom diagnosis, prognosis, or therapy of RA is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc.

As used herein, phrases such as "rheumatoid arthritis patient" or "RA patient" includes subjects, such as mammalian subjects, that would benefit from the administration of a therapy, diagnostic procedure, or preventive treatment for RA. In some aspects, the term "RA patient" refers to a subject that presents one or more symptoms indicative of RA (e.g., pain, stiffness or swelling of joints), or that is screened for RA (e.g., during a physical examination). Alternatively or additionally, the term "RA patient" also encompasses subjects suspected of having RA or who may have one or more risk factors (e.g., age, sex, family history, smoking, etc). The term encompasses subjects that have not been tested for RA as well as subjects that have received an initial diagnosis.

In some aspects of the present disclosure, a subject is a naïve subject. A naïve subject is a subject that has not been administered a RA therapy, for example a therapeutic agent such as a DMARD. In some aspects, a naïve subject has not been treated with a therapeutic agent prior to being diagnosed with RA. In another aspect, a subject has received therapy and/or one or more doses of a therapeutic agent (e.g., a DMARD) prior to being diagnosed as having RA. The therapeutic agent can be a small molecule drug, an antibody, a fusion protein, a corticosteroid, a NSAID (e.g., ibuprofen, naproxen, etc), a DMARD (e.g., methotrexate, leflunomide, chloroquine, hydroxychloroquine, azathioprine, cyclosporine, D-penicillamine, sulfasalazine, minocycline, etc.), a biologic agent (e.g., abatacept, adalimumab, anakinra, certolizumab, etanercept, golimumab, infliximab, rituximab, tofacitinib, or mevralimumab), or a combination thereof.

In one aspect, the therapeutic agent used according to methods disclosed herein is an antibody, e.g., an anti-GM-CSFRα antibody such as mavrilimumab. Accordingly, in some aspects, a subject has received or is a candidate to receive at least one therapeutically effective dose of an antibody (e.g., mavrilimumab). A subject can be administered at least one therapeutically effective dose of an anti-GM-CSFRα antibody if the subject's anti-PAD4 level is below a predetermined anti-PAD4 threshold level, or if anti-PAD4 autoantibodies are absent or their level is low relative to the anti-PAD4 level in one or more control samples. Also, a subject can be deemed eligible to receive at least one therapeutically effective dose of an anti-GM-CSFRα antibody disclosed herein if the subject's level of anti-PAD4 autoantibodies is below a predetermined anti-PAD4 autoantibody threshold level, or if anti-PAD4 autoantibodies are absent or their level is low relative to the anti-PAD4 autoantibody level in one or more control samples.

In some aspects, the presence or absence of anti-PAD4 autoantibodies is based on the lower limit of quantification (LLOQ) for the assay used. In some embodiments, the assay used is taught here. The bioanalytical parameter "Lower limit of quantification" or "LLOQ" is defined as "the lowest amount of an analyte in a sample that can be quantitatively determined with suitable precision and accuracy" (FDA: Guidance for Industry, Bioanalytical Method Validation, May 2001).

The terms "normal" and "healthy" when applied to a subject are used herein interchangeably. They refer to a subject that has not shown any RA symptoms, and that has not been diagnosed with RA or with cartilage or bone injury. Preferably, a normal subject is not on medication affecting RA and has not been diagnosed with any other disease (in particular an autoimmune inflammatory disease). In certain embodiments, normal subjects may have similar sex, age, and/or body mass index as compared with the subject from which the biological sample to be tested was obtained. The term "normal" is also used herein to qualify a sample obtained from a healthy subject.

The term "therapy" as used herein includes any means for curing, mitigating, or preventing RA, including, for example, therapeutic agents, instrumentation, supportive measures, and surgical or rehabilitative procedures. In this respect, the term therapy encompasses any protocol, method and/or therapeutic or diagnostic that can be used in prevention, management, treatment, and/or amelioration of RA.

The term "therapeutic agent" as used herein refers to any therapeutically active substance that is administered to a subject having RA to produce a desired, usually beneficial, effect. The term therapeutic agent includes, e.g., classical low molecular weight therapeutic agents commonly referred to as small molecule drugs and biologics including but not limited to antibodies or active fragments thereof, peptides, protein drugs, protein conjugate drugs, etc. A therapeutic agent can also be a pro-drug, which metabolizes into the desired therapeutically active substance when administered to a subject. In some aspects, the therapeutic agent is a prophylactic agent. In addition, a therapeutic agent can be pharmaceutically formulated.

A "therapeutically effective" amount as used herein is an amount of therapeutic agent that provides some improvement or benefit to a subject having RA. Thus, a "therapeutically effective" amount is an amount that provides some alleviation, mitigation, and/or decrease in at least one clinical symptom of RA. Clinical symptoms associated with RA that can be treated by the methods and systems of the disclosure are well known to those skilled in the art. Further, those skilled in the art will appreciate that the therapeutic effects need not be complete or curative, as long as some benefit is provided to the subject.

As used herein, a "sufficient amount" or "an amount sufficient to" achieve a particular result in a patient having RA refers to an amount of a therapeutic agent (e.g., an antibody such as mavrilimumab) that is effective to produce a desired effect, which is optionally a therapeutic effect (i.e., by administration of a therapeutically effective amount).

The term "biological sample" is used herein in its broadest sense. A biological sample is generally obtained from a subject. A sample may be of any biological tissue or fluid with which biomarkers of the present disclosure may be assayed. Frequently, a sample will be a "clinical sample", i.e., a sample derived from a patient. Such samples include, but are not limited to, bodily fluids which may or may not contain cells, e.g., blood (e.g., whole blood, serum or plasma), urine, synovial fluid, saliva, tissue or fine needle biopsy samples, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, proteins extracted from the sample. Processing of a biological sample may involve one or more of: filtration, distillation, extraction, concentration, inactivation of interfering components, addition of reagents, and the like. In some aspects, the biological sample is a serologic sample and is (or is derived from) whole blood, serum or plasma obtained from a subject.

As used herein, the term "control", when used to characterize a subject, refers to a subject that is healthy or to a patient who has been diagnosed with a specific disease other than RA. The term "control sample" refers to one, or more than one, biological sample that has been obtained from a healthy subject or from a patient diagnosed with a disease other than RA.

In order to apply the methods and systems of the disclosure, samples from a patient can be obtained before or after the administration of a therapy to treat RA. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to the original healthcare provider or yet another healthcare provider, healthcare benefits provider or the patient. Similarly, the determination of the presence or absence of biomarker (e.g., absence or presence of anti-PAD4 autoantibodies) and/or quantification of level of the biomarker (e.g., quantification of the amount of anti-PAD4 autoantibodies), comparisons between levels of biomarker, evaluation of the absence/presence or levels of biomarker, and treatment decisions, can be performed by one or more healthcare providers, healthcare benefits providers, and/or clinical laboratories.

As used herein, the term "healthcare provider" refers to individuals or institutions that directly interact and administer to living subjects, e.g., human patients. Non-limiting examples of healthcare providers include doctors, nurses, technicians, therapists, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to treat RA. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy (e.g., a therapeutic agent that treats RA), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits provider can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

The terms "biomarker" and "marker" are used herein interchangeably. They refer to a predictive factor that is a distinctive indicator of a biological process, biological event, and/or pathologic condition. As used herein, the term biomarker encompasses both clinical markers and biological markers. Thus, in the context of the present invention, the term "biomarker" encompasses anti-PAD4 autoantibodies as well as other RA "biological biomarkers" comprising proteins such as calpastatin, BRAF, C-reactive protein, serum amyloid A, interleukin 6, S100 proteins, osteopontin, rheumatoid factor, matrix metalloprotease 1, matrix metalloprotease 3, hyaluronic acid, sCD14, angiogenesis markers, products of bone, cartilage, or synovium metabolism, EYA4, PDZD2, TNF in blood or synovium, IL-1b, IL-17, rheumatoid factor (RF), anticitrullinated peptide antibodies (ACPA), and combinations thereof. The biological markers disclosed herein include also the genes encoding those proteins (DNA and/or RNA), as well as metabolic products.

The terms "labeled", "detectably labeled," "labeled with a detectable agent," and "labeled with a detectable moiety" are used herein interchangeably. These terms are used to specify that an entity (e.g., full length PAD4 or a PAD4-peptide targeted by autoantibodies) can be visualized, for example, following binding to another entity (e.g., an anti-PAD4 autoantibody). Preferably, a detectable agent or moiety is selected such that it generates a signal which can be measured and whose intensity is related to the amount of bound entity. In array-based methods, a detectable agent or moiety is also preferably selected such that it generates a localized signal, thereby allowing spatial resolution of the signal from each spot on the array. Methods for labeling proteins and polypeptides are well-known in the art. Labeled polypeptides, e.g., labeled PAD4 or fragments thereof, can be prepared by incorporation of or conjugation to a label, that is directly or indirectly detectable by spectroscopic, photochemical, biochemical, immunochemical, electrical, optical, or chemical means, or any other suitable means Suitable detectable agents include, but are not limited to, various ligands, radionuclides, fluorescent dyes, chemiluminescent agents, microparticles, enzymes, colorimetric labels, magnetic labels, and haptens. In some aspects of the present disclosure, recombinant PAD4 or fragments thereof can be labeled with ruthenium to yield luminescent Ru(II) metal complexes.

The term "mavrilimumab" refers to a human lgG4 monoclonal antibody designed to modulate macrophage activation, differentiation and survival by targeting GM-CSFRα as described, for example, in U.S. Pat. Nos. U.S. Pat. Nos. 8,263,075 and 8,506,960, and U.S. Publ. Nos. US20090130093, US20120141464, and US20140079708, all of which are herein incorporated by reference in their entireties. US20140335081 describes the use of mavrilimumab to treat RA. Mavrilimumab, as used herein, encompasses the mavrilimumab antibody comprising a heavy chain of SEQ ID NO: 2 and a light chain of SEQ ID NO: 3, as well as antigen-binding fragments thereof.

Mavrilimumab is a potent neutralizer of the biological activity of GM-CSFRα and, without wishing to be bound by theory, may exert therapeutic effects by binding GM-CSFRα on leukocytes within the synovial joints of RA patients, leading to reduced cell survival and activation. U.S. Pat. No. 8,263,075 reports the isolation and characterization of mavrilimumab and variants of it which share an ability to neutralize the biological activity of GM-CSFRα with high potency. The functional properties of these antibodies are believed to be attributable, at least in part, to binding a Tyr-Leu-Asp-Phe-Gln motif at positions 226 to 230 of human GM-CSFRα (this sequence of amino acids is set forth in SEQ ID NO: 12), thereby inhibiting association between GM-CSFRα and its ligand GM-CSF. The amino acid sequences of the mavrilimumab heavy chain (HC; set forth in SEQ ID NO: 2); light chain (LC; set forth in SEQ ID NO:3); heavy chain variable region (VH; set forth in SEQ ID NO:4); light chain variable region (VL; set forth in SEQ ID NO:5); heavy chain variable region complementarity determining regions (VH-CDR1, VH-CDR2, and VH-CDR3, set forth in SEQ ID NOs: 6, 7 and 8, respectively), and light chain variable region CDRs (VL-CDR1, VL-CDR2, and VL-CDR3; set forth in SEQ ID NOs: 9, 10, and 11 respectively).

The term "PAD4" as used herein refers to peptidyl arginine deiminase, type IV and isoforms thereof. The amino acid sequence of a human PAD4 is found in Uniprot: Q9UM07; and set forth in SEQ ID NO:13). In humans this protein is encoded by the PADI4 gene, and fragments thereof (Jones et al. Curr Opin Drug Discov Devel. 12: 616-627 (2009)). Critical autoantibodies in RA are directed at citrullinated residues on different proteins such as fibrin, filaggrin, fibronectin, enolase and vimentin. Citrullinated proteins are generated by the post-translational conversion of arginine residues to citrulline, a process catalyzed by calcium-dependent peptidyl arginine deiminases (PAD)s.

PAD4 is widely believed to play a role in RA disease onset and progression because RA-associated mutations in the PAD4 gene have been identified in a variety of populations. See, for example, Suzuki et al., Nat. Genet. 34: 395-402 (2003,); Iwamoto et al., Rheumatology 45: 804-807 (2006); Harney et al., Rheumatology 44: 869-872 (2005); and Cantaert et al., Ann. Rheum. Dis. 64: 1316-1320 (2005). PAD4 is not only involved in the generation of citrullinated epitopes, it is in itself a target for RA-specific antibodies. Autoantibodies against PAD4 have been described in RA patients. See, for example, Takizawa et al., Scand. J. Rheumatol. 3: 212-215 (2005); Roth et al., Clin. Exp. Rheumatol.

1: 12-18 (2006); Halvorsen et al., Ann. Rheumatol. Dis. 67: 414-417 (2008); and Zhao et al., J. Rheumatol., 35: 969-974 (2008).

The term "PAD3" as used herein refers to the protein arginine deiminase type 3, and isoforms thereof. The amino acid sequence of a human PAD3 is found in Uniprot Q9ULW8. This protein is encoded in humans by the PADI3 gene.

The term "GM-CSFR" as used herein refers to granulocyte-macrophage colony stimulating-factor (GM-CSF) receptor. GM-CSFR is a member of a highly conserved cytokine receptor super family. GM-CSFR comprises two subunits which result in different affinities for GM-CSF observed on some hematopoietic cells. The first subunit is commonly referred to as the $\alpha_1$ subunit, and is an 85 Kd protein which can bind GM-CSF by itself with low affinity. Multiple other isoforms of the GM-CSFRα chain, some membrane-bound and some soluble, have been described, however the al isoform appears to be the predominant form expressed on the cell surface of neutrophils and macrophages (Crosier et al., Br J Haematol. 98:540-548 (1997)). The extracellular portion of GM-CSFR ai is highly glycosylated. The receptor has a second subunit, the f3 chain, which does not bind to GM-CSF by itself. Rather, it binds GM-CSF when associated with the ai receptor. The terms "GM-CSFRα," "GM-CSFRα," "GM-CSFR alpha" and grammatical variants thereof refer to the $\alpha_1$ subunit of GM-CSFR, this protein may have the amino acid sequence set forth in SEQ ID NO: 1.

II. Anti-PAD4 Autoantibodies as a Clinical Response Biomarker

RA is characterized by the presence of several types of autoantibodies. Autoantibodies directed against PAD4 are present in approximately one-third of RA patients. However, there is currently a poor understanding of the function and potential pathogenic role the anti-PAD4 autoantibodies may have in RA. New therapeutic options, including therapeutic antibodies that specifically bind to human GM-CSFRα such as mavrilimumab are important to address the unmet medical needs of RA patients. Means to identify RA patients likely to have a good clinical response to these antibodies, i.e., a diagnostic or clinical response biomarker, could greatly augment the utility of this novel therapeutic.

We have found that the presence of anti-PAD4 autoantibodies in the serum of RA subjects prior to the initiation of therapy with mavrilimumab is a predictor of clinical response. Anti-PAD4 autoantibody levels have been measured in serum using a novel assay that detects anti-PAD4 antibodies by their ability to bind PAD4. This assay was used to quantify anti-PAD4 autoantibody levels in the baseline serum samples of the RA subjects entered into a clinical study. Statistical analysis showed that RA subjects with anti-PAD4 autoantibody levels below the lowest limit of quantification (LLOQ) of the assay had a significantly increased clinical response to mavrilimumab compared to placebo, while the response to mavrilimumab by subjects with detectable anti-PAD4 autoantibody levels was more comparable to the response to placebo. This finding supports the utility of testing for the presence of anti-PAD4 autoantibodies prior to initiation of mavrilimumab therapy to identify patients who will have a positive clinical outcome if treated with mavrilimumab compared to DMARD standard-of-care therapy. In addition, there are currently no diagnostic tests employed by rheumatologists to aid in the selection of therapy options to treat RA patients. Measuring anti-PAD4 autoantibody levels (through the blood test) to indicate that a patient is likely to have a much better outcome if treated with mavrilimumab than if treated with DMARDs alone is a significant advance in the treatment paradigm for this disease. In some embodiments, the anti-PAD4 autoantibody levels are measured using the novel method taught here.

The term "level", e.g., as in "anti-PAD4 autoantibody level," "anti-PAD4 autoantibody level," "level of anti-PAD4 autoantibodies," "patient's level of anti-PAD4 autoantibodies," and grammatical variants thereof refers to a measurement that is made using any analytical method for detecting presence or expression of anti-PAD4 autoantibodies in a biological sample and that indicates the presence, absence, absolute amount or concentration, relative amount or concentration, titer, expression level, ratio of measured levels, or the like, of, for, or corresponding to anti-PAD4 autoantibodies in the biological sample. The exact nature of the "value" or "level" depends on the specific designs and components of the particular analytical method employed to detect anti-PAD4 autoantibodies.

As used herein with respect to the detection of anti-PAD4 autoantibodies in a sample obtained from a subject, the terms "absent" or "present" refers to whether the level of anti-PAD4 autoantibodies is below or above the lowest limit of quantification (LLOQ) for the analytical method used to detect anti-PAD4 autoantibodies in the biological sample As used herein with reference to anti-PAD4 autoantibodies, the terms "elevated levels," "high levels," and variants thereof refer to a level in a biological sample (e.g., blood serum) that is higher than a control level or range. Thus, the level measured in a particular biological sample can be compared with level or range of levels determined in similar control samples. In some aspects, the control sample would be a sample obtained from a subject with no detectable RA symptoms. In other aspects, the control sample would be a sample obtained from a subject who is seropositive for anti-PAD4 autoantibodies (e.g., a subject with a level of anti-PAD4 autoantibodies in serum that has been determined to be unresponsive to therapy with mavrilimumab). The level of anti-PAD4 autoantibodies is said to be elevated wherein the anti-PAD4 autoantibodies are present in the test sample at a higher level or range than in a control sample. Conversely, as used herein with reference to anti-PAD4 autoantibodies, the terms "lower levels," "low levels," and variants thereof refer to a level in a biological sample (e.g., blood serum) that is lower than a control level or range. Thus, the level of anti-PAD4 autoantibodies is said to be low or lowered wherein the anti-PAD4 autoantibodies are present in the test sample at a lower level or range than in a control sample.

The methods disclosed herein can be carried out using any sample that may contain anti-PAD4 autoantibodies. Convenient samples include, for example, whole blood, blood serum, plasma, peripheral blood mononuclear cell samples, or synovial fluid or synovial tissue. In some aspects, a synovial tissue sample can be obtained from a knee joint or an ankle-joint. In some aspects, anti-PAD4 autoantibodies are measured in a blood serum sample.

In some aspects, the sample can be pretreated as necessary by concentration, or dilution in an appropriate buffer solution, such as phosphate, Tris, or the like, at physiological pH.

Anti-PAD4 autoantibodies can be detected and quantified by any of a number of methods well known to those of skill in the art. These methods include analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, and the like.

In a specific aspect, anti-PAD4 autoantibodies are detected and/or quantified in the biological sample using an immunoassay. While immunoassays for detecting anti-PAD4 autoantibodies are known in the art, an immunoassay for the detection of anti-PAD4 autoantibodies is described herein.

In certain aspects, the immunoassay comprises a sandwich immunoassay, e.g., an enzyme-linked immunosorbent assay (ELISA) or a sandwich electrochemiluminescent (ECL) assay, in which a first PAD4 molecule ("capture PAD4") is attached to a solid support, anti-PAD4 autoantibodies from a sample or standard are allowed to bind to the capture PAD4, and then a second PAD4 molecule ("detection PAD4") is added and detected either by an enzymatic reaction, an ECL reaction, radioactivity, or other detection method. Thus, the immunoassay would measure the anti-PAD4 autoantibody-induced crosslinking of "capture PAD4" and "detection PAD4." In certain aspects in the immunoassay, the capture PAD4 molecule is not bound to a solid support.

The term "attached to a solid support" refers to the immobilization that takes place by attachment to a substrate (e.g., the surface of a well in a plate) by adsorption, covalent binding or by means of a specific binding pair, e.g., by means of the specific interaction of a suitable specific binding pair such as biotin/avidin.

The detection PAD4 can be directly labeled with an enzyme, e.g., horseradish peroxidase or alkaline phosphatase, or can be labeled with a tag that will allow an enzyme to bind. Examples of enzyme labels are e.g. alkaline phosphatase, peroxidase and galactosidase. For example the detection PAD4 can be conjugated to biotin, and the enzyme attached in a subsequent step by allowing enzyme-conjugated streptavidin to bind to the biotin tag. Alternatively the detection PAD4 can be conjugated to a chemiluminescent, fluorescent, or ECL tag. An example of the latter is a ruthenium chelate. Following incubation, the plate can then be washed to remove any unbound detection PAD4.

Detection of the detection PAD4 can be accomplished by methods that vary based on the type of detection system that is used. If the detection PAD4 is tagged with biotin, then enzyme-conjugated streptavidin is added, unbound streptavidin is washed away, and a substrate is added which provides a colorimetric reaction that can be read, e.g., on a spectrophotometer.

Luminescent metal chelates are metal chelates which generate a detectable luminescence reaction. The detection of this luminescence reaction can for example be by measurement of fluorescence (i.e., if the detection PAD4 is conjugated to a ruthenium chelate, fluorescence is measured) or by electrochemiluminescence (i.e., if the detection PAD4 is conjugated to a ruthenium chelate, the plate can be subjected to an electrical current, and light emission is measured).

The metal of these metal chelates is for example a transition metal or a rare earth metal. The metal can be, for example, ruthenium, osmium, rhenium, iridium, rhodium, platinum, indium, palladium, molybdenum, technetium, copper, chromium or tungsten. The ligands which form the metal chelate together with the metal are usually polydentate ligands i.e. ligands with several coordination positions. Polydentate ligands for example comprise aromatic and aliphatic ligands.

In certain aspects, the method directly measures anti-PAD4 autoantibody levels in a patient sample, where absolute levels are calculated by plotting the immunoassay results on a standard curve. The detected signal can then be quantitated based on the various standards and/or controls. By plotting the results on a standard curve, the absolute levels of anti-PAD4 autoantibody in the samples can be calculated, e.g., in ng anti-PAD4/mL or anti-PAD4 units/mL (U/mL).

Based on comparison to known control samples, a "threshold level" can be determined, and test samples that fall above that anti-PAD4 autoantibody threshold level can indicate, for example, that the patient from whom the sample was taken may benefit from treatment with an antibody or antigen-binding fragment thereof that specifically binds to GM-CSFR such as mavrilimumab. Anti-PAD4 autoantibody threshold levels can be predetermined, and in that case they must be matched as to the type of sample (e.g., serum or synovial fluid), the type of RA (e.g., seropositive or seronegative RA), and in some instances, the assay used.

In some aspects, the predetermined threshold level is the lower limit of quantification (LLOQ) of the assay used to detect the presence of anti-PAD4 autoantibodies in a sample. In some aspects, the LLOQ is the LLOQ of the assay presented in Example 1 of the present disclosure. In some aspects, the LLOQ of the assay used to detect the presence of anti-PAD4 autoantibodies in a sample is at least 1,000 U/mL, at least 1,100 U/mL, at least 1,200 U/mL, at least 1,300 U/mL, at least 1,400 U/mL, at least 1,500 U/mL, at least 1,600 U/mL, at least 1,700 U/mL, at least 1,800 U/mL, at least 1,900 U/mL, at least 2,000 U/mL, at least 2,100 U/mL, at least 2,200 U/mL, at least 2,300 U/mL, at least 2,400 U/mL, at least 2,500 U/mL, at least 2,600 U/mL, at least 2,700 U/mL, at least 2,800 U/mL, at least 2,900 U/mL, at least 3,000 U/mL, at least 3,100 U/mL, at least 3,200 U/mL, at least 3,300 U/mL, at least 3,400 U/mL, at least 3,500 U/mL, at least 3,600 U/mL, at least 3,700 U/mL, at least 3,800 U/mL, at least 3,900 U/mL, at least 4,000 U/mL, at least 4,100 U/mL, at least 4,200 U/mL, at least 4,300 U/mL, at least 4,400 U/mL, at least 4,500 U/mL, at least 4,600 U/mL, at least 4,700 U/mL, at least 4,800 U/mL, at least 4,900 U/mL, at least 5000 U/mL, at least 5500 U/mL, at least 6000 U/mL, or at least 6500 U/mL.

In some aspects, the anti-PAD4 autoantibody predetermined threshold level in a sample, e.g., a serum sample, can be at least about 5,000 U/mL, at least about 10,000 U/mL, at least about 15,000 U/mL, at least about 20,000 U/mL, at least about 25,000 U/mL, at least about 30,000 U/mL, at least about 35,000 U/mL, at least about 40,000 U/mL, at least about 45,000 U/mL, at least about 50,000 U/mL, at least about 55,000 U/mL, at least about 60,000 U/mL, at least about 65,000 U/mL, at least about 70,000 U/mL, at least about 75,000 U/mL, at least about 80,000 U/mL, at least about 85,000 U/mL, at least about 90,000 U/mL, at least about 95,000 U/mL, at least about 100,000 U/mL, at least about 110,000 U/mL, at least about 120,000 U/mL, at least about 130,000 U/mL, at least about 140,000 U/mL, at least about 150,000 U/mL, at least about 160,000 U/mL, at least about 170,000 U/mL, at least about 180,000 U/mL, at least about 190,000 U/mL, at least about 200,000 U/mL, at least about 210,000 U/mL, at least about 220,000 U/mL, at least about 230,000 U/mL, at least about 240,000 U/mL, at least about 250,000 U/mL, at least about 260,000 U/mL, at least about 270,000 U/mL, at least about 280,000 U/mL, at least about 290,000 U/mL, or at least about 300,000 U/mL as measured in the sample (e.g., serum) using an immunoassay. In some aspects, the immunoassay is the assay presented in Example 1 of the present disclosure.

The anti-PAD4 autoantibody threshold level can vary based on the nature of the assay, e.g., the capture PAD4 and detection PAD4 used, the source, purity, and composition of the standards, and the like. In one aspect, instead of using an arbitrary threshold level or the LLOQ of the assay to determine whether a patient can benefit from treatment with an antibody or antigen-binding fragment thereof that specifically binds to GM-CSFRα, for example, mavrilimumab, the patient's anti-PAD4 autoantibody levels can be compared to one or more control anti-PAD4 autoantibody levels. According to this aspect, the test sample (e.g., a sample from a patient suffering from RA) is compared to one or more control samples (e.g., samples taken from normal healthy individuals, earlier samples taken from the same patient, samples taken from patients with a subset of the patient's disease, a pre-determined standard amount of isolated anti-PAD4 antibodies, or a combination thereof).

In some aspects, the results can be expressed as a ratio with the control samples to determine a variation in the subject's anti-PAD4 antibody levels compared to the control levels. According to this aspect, the control sample can be a matched pair with the patient sample, e.g., one or more of whole blood if the patient sample is whole blood, serum if the patient sample is serum, plasma if the patient sample is plasma, or synovial fluid if the patient sample is synovial fluid Anti-PAD4 antibody detection assays can be scored (as positive or negative or quantity of analyte) according to standard methods well known to those of skill in the art. The particular method of scoring will depend on the assay format and choice of label. For example, an immunoassay can be scored by visualizing a detectably labeled component (e.g., ruthenylated PAD4 in the immunoassay described in Example 1). A detectable signal (e.g., a luminescent signal above the control or background level) is scored as a positive result, while the absence of a clearly detectable signal is scored as a negative and is known as the LLOQ for the assay. The intensity of the detectable signal can provide a quantitative measure of analyte concentration.

Once determined, an anti-PAD4 antibody level can be recorded in a patient medical record. In some aspects, the methods disclosed herein include making a diagnosis, often a differential diagnosis, based at least in part on the anti-PAD4 antibody level.

As used herein, the term "differential diagnosis" can refer to the determination of whether a patient is susceptible to treatment, is likely to respond to treatment, or is a candidate for treatment with an antibody or antigen-binding fragment thereof that specifically binds to GM-CSFRα (for example mavrilimumab) depending on whether the measured anti-PAD4 antibody level in a sample from the patient sample is below a predetermined threshold level, or is low relative to the anti-PAD4 antibody level in one or more control samples (e.g, in some aspects a patient may be responsive to mavrilimumab treatment even if the patient tests positive for anti-PAD4 antibodies as long as the level of anti-PAD4 antibodies is below a predetermined threshold level). In certain aspects, the predetermined threshold level of anti-PAD4 autoantibodies is the LLOQ of the assay.

In particular aspects, the methods disclosed herein include informing the subject of a result of an assay to detect anti-PAD4 antibodies and/or of a diagnosis based at least in part on the level of anti-PAD4 autoantibodies. The patient can be informed verbally, in writing, and/or electronically.

This diagnosis can also be recorded in a patient medical record. For example, in various aspects, the diagnostic of whether a patient with RA may benefit by treatment with a specific antibody or antigen-binding fragment thereof that specifically binds to GM-CSFRα (e.g., mavrilimumab) is recorded in a medical record. The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and it is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record may be reviewed by a physician in diagnosing the condition.

The medical record can be in paper form and/or can be maintained in a computer-readable medium. The medical record can be maintained by a laboratory, physician's office, a hospital, a healthcare maintenance organization, an insurance company, and/or a personal medical record website. In some aspects, a diagnosis, based at least in part on the level of anti-PAD4 autoantibodies in a sample from a patient, is recorded on or in a medical alert article such as a card, a worn article, and/or a radiofrequency identification (RFID) tag. As used herein, the term "worn article" refers to any article that can be worn on a subject's body, including, but not limited to, a tag, bracelet, necklace, arm band, or head band.

The methods disclosed herein also include prescribing, initiating, and/or altering prophylaxis and/or therapy for RA (in particular, for a subtype of RA such a seropositive RA or seronegative RA in which patients test respectively positive or negative for the presence of autoantibodies such as anti-PAD4 autoantibodies). In some embodiments, the presence of anti-PAD4 autoantibodies is determined using the methods taught here.

In certain aspects, the methods can entail ordering and/or performing one or more additional assays. For example, if an assay indicates that the patient's sample tests negative for the presence of anti-PAD4 autoantibodies, the assay may be repeated to rule out a false negative result, and/or one or more additional assays to determine the presence or absence of anti-PAD4 autoantibodies may be performed to confirm the subject's status. Conversely, if the levels of anti-PAD4 autoantibodies are determined to be elevated, it may be desirable repeat the assay to rule out a false positive result.

A person skilled in the art would understand that anti-PAD4 autoantibody levels can be used according to the methods disclosed herein, including but not limited to treatment, diagnostic, and monitoring methods, as (i) positive selectors, i.e., a specific action would be taken (e.g., treating a patient having RA with mavrilimumab) if the level of anti-PAD4 autoantibodies in a sample taken from the patient is below a predetermined threshold level, below the LLOQ of the detection assay used, or is low relative to the anti-PAD4 autoantibody level in one or more control samples; or (ii) negative selectors, i.e., a specific action would be taken (e.g., cease treating a patient having RA with mavrilimumab) if the level of anti-PAD4 autoantibodies in a sample taken from the patient is above a predetermined threshold level, above the LLOQ of the detection assay used, or is high relative to the anti-PAD4 autoantibody level in one or more control samples; or (iii) both positive and negative selectors, for example, a specific treatment could cease (e.g., DMARD) and a different treatment could commence (e.g., treatment with mavrilimumab) if the anti-PAD4 autoantibody level in a sample taken from the patient is above/below a predetermined threshold level, above/below the LLOQ of the detection assay used, or is high/low relative to the anti-PAD4 autoantibody level in one or more control samples.

III. Methods of Diagnosis and Treatment RA Based on Anti-PAD4 Biomarker Levels This disclosure provides a method of treating an RA patient (or a subject suspected to suffer from RA) comprising administering an antibody or antigen-binding fragment thereof that specifically binds to GM-CSFRα (e.g., mavrilimumab) to the patient if the level of anti-PAD4 autoantibodies in a sample taken from the patient is below the lower limit of quantification (LLOQ) for the detection assay used (e.g., an immunoassay), below a predetermined threshold level, or low relative to the anti-PAD4 autoantibody level in one or more control samples. Also provided is method of treating an RA patient (or a subject suspected to suffer from RA) comprising administering an antibody or antigen-binding fragment thereof that specifically binds to GM-CSFRα (e.g., mavrilimumab) to the patient if (a) the level of anti-PAD4 autoantibodies in a sample taken from the patient is below the LLOQ for the detection assay used, below a predetermined threshold level, or low relative to the anti-PAD4 autoantibody level in one or more control samples and (b) the patient presents a level of at least one additional biomarker in a sample taken from the patient which is above or below a predetermined biomarker threshold level, or is above or below the biomarker level in one or more control samples. In some aspects, the methods further comprise obtaining the sample from the patient and submitting the sample for measurement of the level of anti-PAD4 autoantibodies in the sample. In one aspect, the presence or absence of anti-PAD4 autoantibodies in the sample is measured in an immunoassay, e.g., a chemoluminescence assay using PAD4 attached to a substrate and detectably labeled PAD4 (e.g., ruthenylated PAD4).

This disclosure also provides methods, assays, and kits to facilitate a determination by a healthcare provider, a healthcare benefits provider, or a clinical laboratory to as to whether a patient will benefit from treatment with an antibody or antigen-binding fragment thereof that specifically binds to GM-CSFRα (e.g., mavrilimumab). In some aspects, the antibody or antigen-binding fragment thereof that specifically binds to GM-CSFRα is mavrilimumab, an antibody or fragment thereof that binds to the same GM-CSFRα epitope as mavrilimumab, or an antibody or fragment thereof that competitively inhibits binding of mavrilimumab to GM-CSFRα. The methods, assays, and kits provided herein will also facilitate a determination by a healthcare provider, a healthcare benefits provider, or a clinical laboratory as to whether a patient will benefit from treatment with an antibody or antigen-binding fragment thereof that specifically binds to GM-CSFRα disclosed herein, or known to those of ordinary skill in the art.

The present disclosure provides methods of treating an RA patient (or a subject suspected to suffer from RA) comprising measuring the level of anti-PAD4 autoantibodies in a sample (e.g., a blood serum sample) obtained from a patient having RA; determining whether the patient's level of anti-PAD4 autoantibodies in the sample is above or below the LLOQ for the assay (e.g., an immunoassay); and advising a healthcare provider to administer an antibody or antigen-binding fragment thereof that specifically binds to GM-CSFRα (e.g., mavrilimumab) to the patient if the patient's anti-PAD4 autoantibody level is below the LLOQ for the assay. Conversely, the method would comprise advising a healthcare provider to suspend the administration of an antibody or antigen-binding fragment thereof that specifically binds to GM-CSFRα to the patient if the patient's anti-PAD4 autoantibody level is above the LLOQ for the assay. In certain embodiments, the anti-PAD4 autoantibody level is determined using the assay taught here.

The present disclosure also provides a method of treating an RA patient (or a subject suspected to suffer from RA) comprising submitting a sample taken from the patient for measurement of the level of anti-PAD4 autoantibodies in the sample; and administering an antibody or antigen-binding fragment thereof that specifically binds to GM-CSFRα (e.g., mavrilimumab) to the patient if the patient's anti-PAD4 autoantibody level in the sample is below the LLOQ for the assay. Also provided is a method of treating an RA patient comprising submitting a sample taken from the patient for measurement of the level of anti-PAD4 autoantibodies in the sample; and suspending the administration of an antibody or antigen-binding fragment thereof that specifically binds to GM-CSFRα (e.g., mavrilimumab) to the patient if the patient's anti-PAD4 autoantibody level in the sample is above the LLOQ for the assay.

The present disclosure also provides a method of determining whether to treat a patient diagnosed with RA (or a subject suspected to suffer from RA) with a therapeutic regimen comprising the administration of an antibody or antigen-binding fragment thereof that specifically binds to GM-CSFRα (e.g., mavrilimumab), comprising: measuring, or instructing a clinical laboratory to measure the level of anti-PAD4 autoantibodies in a sample obtained from the patient diagnosed with RA; and treating, or instructing a healthcare provider to treat the patient with a therapeutic regimen comprising the administration of an antibody or antigen-binding fragment thereof that specifically binds to GM-CSFRα (e.g., mavrilimumab) if the patient's anti-PAD4 autoantibody level in the sample is below the LLOQ for the assay. Also provided is a method of determining whether to treat a patient diagnosed with RA with a therapeutic regimen comprising the administration of an antibody or antigen-binding fragment thereof that specifically binds to GM-CSFRα (e.g., mavrilimumab), comprising measuring, or instructing a clinical laboratory to measure the anti-PAD4 level in a sample obtained from the patient diagnosed with rheumatoid arthritis; and suspending the treatment, or instructing a healthcare provider to suspend the treatment of the patient with a therapeutic regimen comprising the administration of an antibody or antigen-binding fragment thereof that specifically binds to GM-CSFRα (e.g., mavrilimumab) if the patient's anti-PAD4 autoantibody level in the sample is above the LLOQ for the assay.

The present disclosure also provides methods of selecting a patient diagnosed with RA (or a subject suspected to suffer from RA) as a candidate for treatment with an antibody or antigen-binding fragment thereof that specifically binds to GM-CSFRα (e.g., mavrilimumab) comprising measuring, or instructing a clinical laboratory to measure the level of anti-PAD4 autoantibodies in a sample obtained from a patient diagnosed with RA; and treating, or instructing a healthcare provider to treat the patient with an antibody or antigen-binding fragment thereof that specifically binds to GM-CSFRα (e.g., mavrilimumab) if the patient's anti-PAD4 autoantibody level in the sample is below the LLOQ for the assay. Also provided is method of selecting a patient diagnosed with RA as a candidate for treatment with an antibody or antigen-binding fragment thereof that specifically binds to GM-CSFRα (e.g., mavrilimumab) or an alternative RA treatment comprising: measuring, or instructing a clinical laboratory to measure the anti-PAD4 level in a sample obtained from a patient diagnosed with rheumatoid arthritis; and instructing a healthcare provider to suspend the treatment of the patient with an antibody or antigen-binding fragment thereof that specifically binds to GM-CSFRα (e.g., mavrilimumab) or select an alternative treatment if the patient's anti-PAD4 autoantibody level in the sample is above the LLOQ for the assay.

In some aspects of the methods described above, instead of using the LLOQ of the assay as the criterion to make a treatment decision, alternative criteria can be used such a determining whether the measured levels of anti-PAD4 autoantibodies are above or below a predetermined threshold level, or whether they are high or low relative to the anti-PAD4 autoantibody level in one or more control samples.

In some aspects, the level of anti-PAD4 autoantibodies in a sample obtained from an RA patient or a subject suspected to have RA is measured in an immunoassay. In certain aspects, the immunoassay is performed on a sample obtained from the patient or subject suspected to have RA, by the healthcare professional treating the patient or subject, e.g., using an immunoassay as described herein, formulated as a "point of care" diagnostic kit. In some aspects, a sample is obtained from the patient and is submitted, e.g., to a clinical laboratory, for measurement of the level of anti-PAD4 autoantibodies in the sample according to the healthcare professional's instructions, e.g., using an immunoassay as described herein. In certain aspects, the clinical laboratory performing the assay will advise the healthcare provide as to whether the patient can benefit from treatment with an antibody or antigen-binding fragment thereof that specifically binds to GM-CSFR (e.g., mavrilimumab) or select an alternative treatment based on whether the patient's level of anti-PAD4 autoantibodies is above or below the LLOQ of the immunoassay, above or below a predetermined anti-PAD4 autoantibody threshold value or is elevated relative to the level of anti-PAD4 autoantibodies in one or more control samples.

In certain aspects, this disclosure provides a method of treating an RA patient or a subject suspected of having RA over a period of time, comprising: measuring a first level of anti-PAD4 autoantibodies in a first sample taken from the patient/subject, or submitting a first sample taken from the patient/subject for measurement of a first level of anti-PAD4 autoantibodies in the sample, and administering an antibody or antigen-binding fragment thereof that specifically binds to GM-CSFR (e.g., mavrilimumab) if the patient's level of anti-PAD4 autoantibodies is above or below the LLOQ of the immunoassay, above or below a predetermined anti-PAD4 autoantibody threshold value or is elevated relative to the level of anti-PAD4 autoantibodies in one or more control samples. The test can be performed by a healthcare provider or a clinical laboratory as noted above.

According to this aspect, the method can further comprise: measuring a second level of anti-PAD4 autoantibodies in a second sample taken from the patient, or submitting a second sample taken from the patient for measurement of a second level of anti-PAD4 autoantibodies in the sample, wherein the patient's level of anti-PAD4 autoantibodies is obtained by comparing the first and second levels of anti-PAD4 autoantibodies in the patient, and altering the dose, e.g., increasing or maintaining the amount or frequency of the antibody or antigen-binding fragment thereof that specifically binds to GM-CSFR (e.g., mavrilimumab) administered to the patient, or even discontinuing therapy with the antibody or antigen-binding fragment thereof that specifically binds to GM-CSFR (e.g., mavrilimumab) if the patient's anti-PAD4 autoantibody level in the second sample is higher than the corresponding level in the first sample, or maintaining or reducing the amount or frequency of the antibody or antigen-binding fragment thereof that specifically binds to GM-CSFR (e.g., mavrilimumab) administered to the patient if the patient's anti-PAD4 autoantibody level in the second sample is lower than or about the same as the corresponding level in the first sample.

In certain aspects, results of an immunoassay as provided herein can be submitted to a healthcare benefits provider for determination of whether the patient's insurance will cover treatment with an antibody or antigen-binding fragment thereof that specifically binds to GM-CSFR (e.g., mavrilimumab).

In certain aspects, the patient has been treated or is being treated with one or more additional medications (e.g., DMARDS), either before, during, or after administration of an antibody or antigen-binding fragment thereof that specifically binds to GM-CSFRα (e.g., mavrilimumab). Various other medications useful for treating RA are described elsewhere herein or are known in the art. In certain aspects the patient has been treated, continues to be treated, or will be treated with one or more additional medications comprising, e.g., a DMARD or a combination thereof. In some aspects, DMARDs are selected from abatacept, adalimumab, azathioprine, chloroquine, hydroxychloroquine, ciclosporin, D-penicillamine, etanercept, golimumab, infliximab, leflunomide, methotrexate, minocycline, rituximab, sulfasalazine, and combinations thereof.

In some aspects, the antibody or antigen-binding fragment thereof that specifically binds to GM-CSFRα comprises mavrilimumab or an antigen-binding fragment thereof. In some aspects, the antibody or antigen-binding fragment thereof that specifically binds to GM-CSFRα consists or consists essentially of mavrilimumab or an antigen-binding fragment thereof. In some aspects, the antibody or antigen-binding fragment thereof that specifically binds to GM-CSFRα specifically binds to the same epitope as mavrilimumab. In some aspects, the antibody or antigen-binding fragment thereof that specifically binds to GM-CSFRα specifically competes with mavrilimumab for binding to the same epitope. In some aspects, the antibody or antigen-binding fragment thereof that specifically binds to GM-CSFRα comprises the heavy chain variable region (VH) comprising the amino acid sequence set forth in SEQ ID NO: 4, and/or the light chain variable region (VL) comprising the amino acid sequence set forth in SEQ ID NO: 5. In some aspects, the antibody or antigen-binding fragment thereof that specifically binds to GM-CSFRα comprises at least one of the complementarity determining regions whose amino acid sequence is set forth in SEQ ID NOS: 6-11. In some aspects, the antibody or antigen-binding fragment thereof that specifically binds to GM-CSFRα comprises the CDRs whose amino acid sequence is set forth in SEQ ID NOS: 6-11.

In some aspects, the samples used in the methods disclosed herein are taken from a patient and comprise one or more of whole blood, serum, plasma, or synovial fluid.

In some aspects, in addition to the determination of the level of anti-PAD4 autoantibodies, the methods disclosed herein can further comprise determining, submitting a sample taken from the patient for determination, or instructing a clinical laboratory to determine the expression level or activity of one or more biological biomarkers, to determine one or more clinical biomarkers (clinical status marker), or a combination thereof.

In some aspects, the antibody or antigen-binding fragment thereof that specifically binds to GM-CSFRα is administered at a fixed dose. In some specific aspects, the antibody or antigen-binding fragment thereof that specifically binds to GM-CSFRα is mavrilimumab and the fixed dose is at least 30 mg/dose, at least 100 mg/dose, or at least 150 mg/dose. In some aspects, the antibody or antigen-binding fragment thereof that specifically binds to GM-CSFRα, e.g., mavrilimumab, is administered in two or more doses. In some aspects, the antibody or antigen-binding fragment thereof that specifically binds to GM-CSFRα, e.g., mavrilimumab, is administered weekly, biweekly or monthly. In some aspects, the antibody or antigen-binding fragment thereof that specifically binds to GM-CSFRα, e.g., mavrilimumab, is administered intravenously, intramuscularly, subcutaneously, or a combination thereof.

IV. Anti-PAD4 Autoantibody Detection Assays and Kits

This disclosure also provides kits for detecting anti-PAD4 autoantibodies in a sample from a RA patient, for example, through an immunoassay method. Such kits can comprise containers, each with one or more of the various reagents (e.g., in concentrated form) utilized in the method, including, for example, labeled and unlabeled PAD4, and anti-PAD4 autoantibody controls.

PAD4 or a fragment thereof capable of binding to anti-PAD4 autoantibodies can be provided already attached to a solid support. Labeled PAD4 or a fragment thereof capable of binding to anti-PAD4 autoantibodies can be provided already conjugated to a detectable label, e.g., biotin or a ruthenium chelate. The kit can also provide reagents for coupling a detectable label to PAD4 or a fragment thereof capable of binding to anti-PAD4 autoantibodies (as well as the label itself), buffers, and/or reagents, and instrumentation to support the practice of the assays provided herein. A kit provided according to this disclosure can further comprise suitable containers, plates, and any other reagents or materials necessary to practice the assays provided herein.

A kit provided according to this disclosure can also comprise brochures or instructions describing the process. For anti-PAD4 autoantibody detection immunoassays, the immunoassay process comprises a first PAD4 molecule or a fragment thereof that can be recognized by anti-PAD4 autoantibodies ("capture PAD4"), and a second PAD4 molecule or a fragment thereof that can be recognized by anti-PAD4 autoantibodies, wherein the second PAD4 is detectable, for example, by incorporating a fluorescent moiety ("detection PAD4").

The immunoassay can be performed by methods provided herein or methods well known and understood by those of ordinary skill in the art. In one aspect, the immunoassay comprises attaching the capture PAD4 to a support; applying the test sample or a control sample, allowing anti-PAD4 autoantibodies, if present in the sample, to bind to the capture PAD4; applying the detection PAD4, which can bind to anti-PAD4 autoantibodies already bound to the capture PAD4; and measuring the amount of detection PAD4 bound to anti-PAD4 autoantibodies. In certain aspects, the assay can further include washing steps, blocking steps and incubation steps.

Test kits can include instructions for carrying out one or more anti-PAD4 autoantibody detection assays, e.g., immunoassays. Instructions included in the kits can be affixed to packaging material or can be included as a package insert. While the instructions are typically written or printed materials they are not limited to such. Any medium capable of storing such instructions and communicating them to an end user is contemplated. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

V. Computer Methods and Software

The methods disclosed herein can comprise collecting or otherwise obtaining a biological sample and performing an analytical method to detect and measure anti-PAD4 autoantibody levels alone or in combination with other biomarkers, e.g., biological biomarker or clinical biomarker.

Biological biomarkers that can be combined with anti-PAD4 autoantibody levels include calpastatin, BRAF, C-reactive protein, serum amyloid A, interleukin 6, S100 proteins, osteopontin, rheumatoid factor, matrix metalloprotease 1, matrix metalloprotease 3, hyaluronic acid, sCD14, angiogenesis markers, products of bone, cartilage, or synovium metabolism, EYA4, PDZD2, TNF in blood or synovium, IL-1b, IL-17, rheumatoid factor (RF), anticitrullinated peptide antibodies (ACPA), and combinations thereof. In some aspects, biological biomarkers that can be combined with anti-PAD4 autoantibody levels include TNFRSF17; immunoglobulin J polypeptide, linker protein for immunoglobulin alpha and mu polypeptides (IGJ); POU class 2 associating factor 1 (POU2AF1); Deri-like domain family, member 3 (DERL3); Fc receptor-like 5 (FCRL5); plasma cell-induced ER protein 1 (PACAP); prepronociceptin (PNOC); secreted phosphoprotein 1 (SPP1); interferon regulatory factor 4 (IRF4); lymphocyte transmembrane adaptor 1 (LAX1); ELL associated factor 2 (EAF2); pim-2 oncogene (PIM2); actin, alpha 1, skeletal muscle (ACTA1); Myosin, heavy chain 3, skeletal muscle, embryonic (MYH2); myosin, heavy chain 1, skeletal muscle, adult (MYH1); cysteine and glycine-rich protein 3 (CSRP3); actinin, alpha 2 (ACTN2); troponin I type 2 (TNNI2); cytochrome P450, family 26, subfamily B, polypeptide 1 (CYP26B1); titin-cap (TCAP), and combinations thereof. See, e.g., U.S. Publ. Nos. US20030027136, US20070231791, which are herein incorporated by reference in their entireties.

Anti-PAD4 autoantibody levels or normalized scores derived from measured anti-PAD4 autoantibody levels can be used alone (e.g., for treatment, diagnostic, prognostic, or monitoring purposes), or in combination with levels or normalized scores derived from other biomarkers (e.g., a panel a genes used to derive a gene signature). These scores can also be combined with scores corresponding, for example, to clinical biomarkers such as (i) gender, (ii) age, (iii) body mass index, (iv) smoking status, (v) concomitant drugs, (vi) health assessment quality (HAQ), (vii) disease activity score 28 joints (DAS28), or a combination of two or more to yield a diagnostic score. In this approach, the diagnostic score may be a single number determined from the sum of all the marker calculations that is compared to a preset anti-PAD4 autoantibody threshold value that is an indication of the presence or absence of disease. Or the diagnostic score may be a series of bars that each represent a biomarker value and the pattern of the responses may be compared to a pre-set pattern for determination of the presence or absence of disease.

At least in some aspects of the methods described herein, the complexity of the calculations involved may require that a method comprising the use of anti-PAD4 autoantibodies as a biomarker be implemented with the use of a computer. In some aspects, the computer system comprises hardware elements that are electrically coupled via bus, including a processor, input device, output device, storage device, computer-readable storage media reader, communications system, processing acceleration (e.g., DSP or special-purpose processors), and memory. The computer-readable storage media reader can be further coupled to computer-readable storage media, the combination comprehensively representing remote, local, fixed and/or removable storage devices plus storage media, memory, etc. for temporarily and/or more permanently containing computer-readable information, which can include storage device, memory and/or any other such accessible system resource.

A single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. Customized hardware might also be utilized and/or particular elements might be implemented in hardware, software or both. Further, while connection to other computing devices such as network input/output devices (not shown) may be employed, it is to be understood that wired, wireless, modem, and/or other connection or connections to other computing devices might also be utilized.

In one aspect, the system further comprises one or more devices for providing input data to the one or more processors. The system further comprises a memory for storing a data set of ranked data elements. In another aspect, the device for providing input data comprises a detector for detecting the characteristic of the data element, e.g., such as a fluorescent plate reader, mass spectrometer, or gene chip reader.

The system additionally may comprise a database management system. User requests or queries can be formatted in an appropriate language understood by the database management system that processes the query to extract the relevant information from the database of training sets. The system may be connectable to a network to which a network server and one or more clients are connected. The network may be a local area network (LAN) or a wide area network (WAN), as is known in the art. Preferably, the server includes the hardware necessary for running computer program products (e.g., software) to access database data for processing user requests. The system can be in communication with an input device for providing data regarding data elements to the system (e.g., expression values). In one aspect, the input device can include a gene expression profiling system including, e.g., a mass spectrometer, gene chip or array reader, and the like.

Some aspects described herein can be implemented so as to include a computer program product. A computer program product may include a computer readable medium having computer readable program code embodied in the medium for causing an application program to execute on a computer with a database. As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements.

Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one aspect, a computer program product is provided to implemented the treatment, diagnostic, prognostic, or monitoring methods disclosed herein, for example, to determine whether to administer an antibody or antigen-binding fragment thereof that specifically binds to GM-CSFRα (e.g., mavrilimumab) to a patient in need thereof if anti-PAD4 autoantibodies are present in a sample taken from the patient, or if the level of anti-PAD4 autoantibodies in a sample taken from the patient is above a predetermined anti-PAD4 autoantibodies threshold level.

The computer program product includes a computer readable medium embodying program code executable by a processor of a computing device or system, the program code comprising:

code that retrieves data attributed to a biological sample from a subject, wherein the data comprises anti-PAD4 autoantibodies level values (presence/absence, amount, or data otherwise derived from these level values) alone or in combination with values corresponding to other biomarkers in the biological sample (e.g., biological marker or clinical markers), and code that executes a classification method that indicates, e.g., whether to administer an antibody or antigen-binding fragment thereof that specifically binds to GM-CSFRα (e.g., mavrilimumab) to a patient in need thereof.

While various aspects have been described as methods or apparatuses, it should be understood that aspects can be implemented through code coupled with a computer, e.g., code resident on a computer or accessible by the computer. For example, software and databases could be utilized to implement many of the methods discussed above. Thus, in addition to aspects accomplished by hardware, it is also noted that these aspects can be accomplished through the use of an article of manufacture comprised of a computer usable medium having a computer readable program code embodied therein, which causes the enablement of the functions disclosed in this description. Therefore, it is desired that aspects also be considered protected by this patent in their program code means as well.

Furthermore, some aspects can be code stored in a computer-readable memory of virtually any kind including, without limitation, RAM, ROM, magnetic media, optical media, or magneto-optical media. Even more generally, some aspects could be implemented in software, or in hardware, or any combination thereof including, but not limited to, software running on a general purpose processor, microcode, PLAs, or ASICs.

It is also envisioned that some aspects could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

SPECIFIC EMBODIMENTS

Embodiment 1

A method of treating a rheumatoid arthritis patient comprising administering an antibody or antigen-binding fragment thereof that specifically binds to human granulocyte macrophage colony-stimulating factor receptor alpha (GM-CSFRα) to the patient if the level of anti-peptidylarginine deiminase 4 (anti-PAD4) autoantibodies in a sample taken from the patient is below the lower limit of quantification (LLOQ) for the assay.

Embodiment 2

A method of treating a rheumatoid arthritis patient comprising administering an antibody or antigen-binding fragment thereof that specifically binds to GM-CSFRα to the patient if the level of anti-PAD4 in a sample taken from the patient is below the LLOQ for the assay, and the patient presents a level of at least one additional biomarker in a sample taken from the patient which is above or below a predetermined biomarker threshold level, or is above or below the biomarker level in one or more control samples.

Embodiment 3

The method of embodiments 1 or 2, wherein a sample is obtained from the patient and is submitted for measurement of the level of anti-PAD4 autoantibodies in the sample.

Embodiment 4

A method of treating a rheumatoid arthritis patient comprising submitting a sample taken from the patient for measurement of the anti-PAD4 autoantibody level in the sample; and administering an antibody or antigen-binding fragment thereof that specifically binds to GM-CSFRα to the patient if the patient's anti-PAD4 autoantibody level in the sample is below the LLOQ for the assay.

Embodiment 5

A method of treating a rheumatoid arthritis patient comprising submitting a sample taken from the patient for measurement of the anti-PAD4 autoantibody level in the sample; and suspending the administration of an antibody or antigen-binding fragment thereof that specifically binds to GM-CSFRα to the patient if the patient's anti-PAD4 autoantibody level in the sample is above the LLOQ for the assay.

Embodiment 6

A method of treating a rheumatoid arthritis patient comprising measuring the anti-PAD4 autoantibody level in a sample obtained from a patient having rheumatoid arthritis; determining whether the patient's anti-PAD4 autoantibody level in the sample is above or below the LLOQ for the assay; and advising a healthcare provider to administer an antibody or antigen-binding fragment thereof that specifically binds to GM-CSFRα to the patient if the patient's anti-PAD4 autoantibody level is below the LLOQ for the assay.

Embodiment 7

A method of treating a rheumatoid arthritis patient comprising measuring the anti-PAD4 autoantibody level in a sample obtained from a patient having rheumatoid arthritis; determining whether the patient's anti-PAD4 autoantibody level in the sample is below the LLOQ for the assay; and advising a healthcare provider to suspend the administration of an antibody or antigen-binding fragment thereof that specifically binds to GM-CSFRα to the patient if the patient's anti-PAD4 autoantibody level is above the LLOQ for the assay.

Embodiment 8

A method of treating a rheumatoid arthritis patient comprising submitting a sample taken from the patient for measurement of the anti-PAD4 autoantibody level in the sample; and administering an antibody or antigen-binding fragment thereof that specifically binds to GM-CSFRα to the patient if the patient's anti-PAD4 autoantibody level in the sample is below the LLOQ for the assay.

Embodiment 9

A method of treating a rheumatoid arthritis patient comprising submitting a sample taken from the patient for measurement of the anti-PAD4 autoantibody level in the sample; and suspending the administration of an antibody or antigen-binding fragment thereof that specifically binds to GM-CSFRα to the patient if the patient's anti-PAD4 autoantibody level in the sample is above the LLOQ for the assay.

Embodiment 10

A method of determining whether to treat a patient diagnosed with rheumatoid arthritis with a therapeutic regimen comprising the administration of an antibody or antigen-binding fragment thereof that specifically binds to GM-CSFRα, comprising: measuring, or instructing a clinical laboratory to measure the anti-PAD4 autoantibody level in a sample obtained from the patient diagnosed with rheumatoid arthritis; and treating, or instructing a healthcare provider to treat the patient with a therapeutic regimen comprising the administration of an antibody or antigen-binding fragment thereof that specifically binds to GM-CSFRα if the patient's anti-PAD4 autoantibody level in the sample is below the LLOQ for the assay.

Embodiment 11

A method of determining whether to treat a patient diagnosed with rheumatoid arthritis with a therapeutic regimen comprising the administration of an antibody or antigen-binding fragment thereof that specifically binds to GM-CSFRα, comprising: measuring, or instructing a clinical laboratory to measure the anti-PAD4 autoantibody level in a sample obtained from the patient diagnosed with rheumatoid arthritis; and suspending the treatment, or instructing a healthcare provider to suspend the treatment of the patient with a therapeutic regimen comprising the administration of an antibody or antigen-binding fragment thereof that specifically binds to GM-CSFRα if the patient's anti-PAD4 autoantibody level in the sample is above the LLOQ for the assay.

Embodiment 12

A method of selecting a patient diagnosed with rheumatoid arthritis as a candidate for treatment with an antibody or antigen-binding fragment thereof that specifically binds to GM-CSFRα comprising: measuring, or instructing a clinical laboratory to measure the anti-PAD4 autoantibody level in a sample obtained from a patient diagnosed with rheumatoid arthritis; and treating, or instructing a healthcare provider to treat the patient with an antibody or antigen-binding fragment thereof that specifically binds to GM-CSFRα if the patient's anti-PAD4 level in the sample is below the LLOQ for the assay.

Embodiment 13

A method of selecting a patient diagnosed with rheumatoid arthritis as a candidate for treatment with an antibody or antigen-binding fragment thereof that specifically binds to GM-CSFRα comprising: measuring, or instructing a clinical laboratory to measure the anti-PAD4 autoantibody level in a sample obtained from a patient diagnosed with rheumatoid arthritis; and instructing a healthcare provider to suspend the treatment of the patient with an antibody or antigen-binding fragment thereof that specifically binds to GM-CSFRα or select an alternative treatment if the patient's anti-PAD4 autoantibody level in the sample is above the LLOQ for the assay.

Embodiment 14

The method according to any one of embodiments 1 to 13, wherein the antibody or antigen-binding fragment thereof that specifically binds to GM-CSFRα comprises mavrilimumab or an antigen-binding fragment thereof.

Embodiment 15

The method according to any one of embodiments 1 to 13, wherein the antibody or antigen-binding fragment thereof that specifically binds to GM-CSFRα consists of mavrilimumab or an antigen-binding fragment thereof.

Embodiment 16

The method according to any one of embodiments 1 to 13, wherein the antibody or antigen-binding fragment thereof that specifically binds to GM-CSFRα specifically binds to the same epitope as mavrilimumab.

Embodiment 17

The method according to any one of embodiments 1 to 13, wherein the antibody or antigen-binding fragment thereof that specifically binds to GM-CSFRα specifically competes with mavrilimumab for binding to the same epitope.

Embodiment 18

The method according to any one of embodiments 1 to 13, wherein the antibody or antigen-binding fragment thereof that specifically binds to GM-CSFRα comprises a heavy chain variable region having the amino acid sequence set forth in SEQ ID NO: 4 and/or a light chain variable region having the amino acid sequence set forth in SEQ ID NO: 5.

Embodiment 19

The method according to any one of embodiments 1 to 13, wherein the antibody or antigen-binding fragment thereof that specifically binds to GM-CSFRα comprises at least one of the complementarity determining regions having the amino acid sequence set forth in SEQ ID NOS: 6 to 11.

Embodiment 20

The method according to any one of embodiments 1 to 13, wherein the antibody of antigen-binding fragment thereof that specifically binds to GM-CSFRα comprises the CDRs having the amino acid sequences set forth in SEQ ID NOs: 6 to 11.

Embodiment 21

The method of any one of embodiments 1 to 20, wherein the patient has been treated with one or more additional Disease-modifying antirheumatic drugs (DMARDs), either before, during, or after administration of an antibody or antigen-binding fragment thereof that specifically binds to GM-CSFRα.

Embodiment 22

The method according to embodiment 21, wherein the DMARD is selected from abatacept, adalimumab, azathioprine, chloroquine, hydroxychloroquine, ciclosporin, D-penicillamine, etanercept, golimumab, infliximab, leflunomide, methotrexate, minocycline, rituximab, sulfasalazine, and combinations thereof.

Embodiment 23

The method according any one of embodiments 1 to 22, wherein the sample obtained from the patient comprises one or more of whole blood, blood serum, plasma, or synovial fluid.

Embodiment 24

The method according to embodiment 23, wherein the sample obtained from the patient is blood serum.

Embodiment 25

The method according to any one of embodiments 1 to 24, further comprising determining, submitting a sample taken from the patient for determination, or instructing a clinical laboratory to determine the expression level or activity of one or more additional biomarkers, or determine at least one clinical status marker, or a combination thereof.

Embodiment 26

The method according to any one of embodiments 1 to 25, wherein the antibody or antigen-binding fragment thereof that specifically binds to GM-CSFRα is administered at a fixed dose.

Embodiment 27

The method according to embodiment 26, wherein the antibody or antigen-binding fragment thereof that specifically binds to GM-CSFRα is administered at a fixed dose of at least 150 mg/dose.

Embodiment 28

The method according to embodiments 1 to 27, wherein the patient's anti-PAD4 autoantibody level is measured in an immunoassay, an agglutination assay, or a homogeneous assay.

Embodiment 29

The method according to embodiment 28, wherein the patient's anti-PAD4 autoantibody level is measured in an immunoassay, and the immunoassay employs detectably labeled PAD4.

Embodiment 30

The method according to embodiment 29, wherein the detectably labeled PAD4 is ruthenylated PAD4.

Embodiment 31

The method according to any one of embodiments 28 to 30, wherein the immunoassay detects anti-PAD4-autoantibody bound to PAD4.

Embodiment 32

An assay for the detection of anti-PAD4 autoantibodies comprising a first PAD4 molecule or a fragment thereof that can be recognized by anti-PAD4 autoantibodies, and a second PAD4 molecule or a fragment thereof that can recognize anti-PAD4 autoantibodies, wherein the second PAD4 molecule is detectable.

Embodiment 33

The assay according to embodiment 32, wherein a fluorescent moiety is incorporated into the detectable PAD4.

Embodiment 34

The assay according to embodiment 33, wherein the fluorescent moiety is ruthenium.

Embodiment 35

A method of treating a rheumatoid arthritis patient comprising measuring the levels of anti-PAD4 autoantibodies in a sample from the patient by using the assay according to any one of embodiments 32 to 34, and administering an antibody or antigen-binding fragment thereof that specifically binds to GM-CSFRα to the patient if the level of anti-PAD4 autoantibodies in the sample from the patient is below the lower limit of quantification (LLOQ) for the assay.

Embodiment 36

A method of treating a rheumatoid arthritis patient comprising administering an antibody or antigen-binding fragment thereof that specifically binds to GM-CSFRα to the patient if the level of anti-PAD4 in a sample taken from the patient is below the LLOQ for the assay of any one of embodiments 32 to 34, and the patient presents a level of at least one additional biomarker in a sample taken from the patient which is above or below a predetermined biomarker threshold level, or is above or below the biomarker level in one or more control samples.

Embodiment 37

A method for determining the amount of anti-PAD4 autoantibodies in a sample by contacting a capture PAD4 to the test sample or a control sample, allowing anti-PAD4 autoantibodies, if present in the sample, to bind to the capture PAD4; applying a detection PAD4, which can bind to anti-PAD4 autoantibodies already bound to the capture PAD4; and measuring the amount of detection PAD4 bound to anti-PAD4 autoantibodies. In certain aspects, the assay can further include washing steps, blocking steps and incubation steps.

All patents and publications referred to herein are expressly incorporated by reference in their entireties.

Aspects of the present disclosure can be further defined by reference to the following non-limiting examples, which describe in detail an assay for the detection of anti-PAD4 autoantibodies, and use of the assay to detect the presence of anti-PAD4 autoantibodies in clinical samples. It will be apparent to those skilled in the art that many modifications, both to materials and methods, can be practiced without departing from the scope of the present disclosure.

EXAMPLES

Example 1

Anti-PAD4 Autoantibody Assay Protocol

MSD standard plates (available from Meso Scale Discovery) were coated with recombinant PAD4 (2 µg/mL in PBS; 50 µL/well; available from Cayman Chemical Company, Ann Arbor, Mich.), and were incubated overnight at 4° C. The plates were washed three times with 200 µL/well wash buffer (PBS/0.05% TWEEN-20®). Following washing, 150 µL/well block buffer (e.g., PBS/0.05% TWEEN-20®/0.2% I-Block Buffer (available from Applied Biosystems, Carlsbad, Calif.) was added to each well, and the plates were incubated for 1-4 hours at room temperature. The plates were then washed three times as noted above.

For the standard curve, anti-PAD4 autoantibody EIA standard (available from Cayman Chemical Company), was serially diluted in block buffer. Serum samples to be tested for anti-PAD4 autoantibody levels were diluted in block buffer—for example, serum samples from subjects were diluted, e.g., 1:16 in block buffer. Twenty-five microliters (25 µL) of each standard or diluted sample was added to the plates, and the plates were incubated for 1 hour at room temperature with gentle shaking on a plate shaker. Again, the plates were washed three times as noted above. Following washing, ruthenylated recombinant PAD4 (25 µL of a 2 µg/ml solution) was added to each well, and the plates were incubated for 1 hour at room temperature with gentle shaking on a plate shaker. Again, the plates were washed three times as noted above. Following washing, 150 µL 1×MSD Read Buffer (available from Meso Scale Discovery, Rockville, Md.) was added to each well. Finally the plates were read on a MSD plate reader (available from Meso Scale Discovery).

Example 2

Detection of Anti-PAD4 Autoantibodies in Serum of Rheumatoid Arthritis Subjects

This example demonstrates that the anti-PAD4 autoantibody assay provided in this disclosure can be used to detect anti-PAD4 auto-antibodies in the serum of subjects with rheumatoid arthritis. Serum samples collected at baseline (at time of study entry) of subjects in three independent clinical trials of mavrilimumab were tested using the anti-PAD4 autoantibody assay of Example 1. The FIG. 1 shows the measured levels of anti-PAD4 autoantibodies in all subjects tested from each of the three clinical trials. A similar frequency of subjects had detectable anti-PAD4 autoantibodies (defined as above the LLOQ for the assay of 5000 U/mL) in the three studies, with 32% (Study A), 39% (Study B) and 42% (Study C) of subjects testing positive as shown below in TABLE 1.

TABLE 1

Anti-PAD4 Autoantibody Levels in RA Subject Serum

| Study | Status | n | Percent | Mean [Anti-Pad4 Ab] U/mL |
|---|---|---|---|---|
| A | Anti-PAD4+ | 104 | 32 | 268,741 |
|   | Anti-PAD4− | 219 | 68 | N/A |
| B | Anti-PAD4+ | 111 | 39 | 214,980 |
|   | Anti-PAD4− | 177 | 61 | N/A |
| C | Anti-PAD4+ | 57 | 42 | 213,881 |
|   | Anti-PAD4− | 80 | 58 | N/A |

Example 3

Anti-PAD3 Autoantibody Assay Protocol

MSD standard plates (available from Meso Scale Discovery) were coated with recombinant PAD3 (2 µg/mL in PBS; 25 µL/well; available from SignalChem, Richmond, British Columbia, Canada) and were incubated overnight at 4° C. The plates were washed three times with 200 µL/well wash buffer (PBS/0.05% TWEEN-20®). Following washing, 150 µL/well block buffer (e.g., PBS/0.05% TWEEN-20®/0.2% I-Block Buffer (available from Applied BioSystems, Carlsbad, Calif.) was added to each well, and the plates were incubated for 1-4 hours at room temperature. The plates were then washed three times as noted above.

For the standard, an RA serum sample positive for anti-PAD3 autoantibody was diluted 1:64 in block buffer. Serum samples to be tested for anti-PAD3 autoantibody levels were diluted in block buffer—for example, serum samples from subjects were diluted, e.g., 1:4 or 1:64 or 1:1024 in block buffer. Twenty-five microliters (25 µL) of each standard or diluted sample was added to the plates, and the plates were incubated for 1 hour at room temperature with gentle shaking on a plate shaker. Again, the plates were washed three times as noted above. Following washing, biotinylated human His10x_Avitag_Human PAD3 (25 µL of a 2 µg/ml solution) was added to each well, and the plates were incubated for 1 hour at room temperature with gentle shaking on a plate shaker. Again, the plates were washed three times as noted above. Following washing, streptavidin SulfoTag (15 µL of a 0.5 µg/ml solution) was added to each well and incubated for 30 min at room temperature. Again, the plates were washed three times as noted above. Following washing, 150 µL 1×MSD Read Buffer (available from Meso Scale Discovery, Rockville, Md.) was added to each well. Finally the plates were read on a MSD plate reader (available from Meso Scale Discovery). Tested samples were determined to be positive if the detected ECL counts for that sample were above the LLOQ for the assay (a ratio of detected ECL counts in the tested serum sample: ECL counts in a negative control sample ≥1.37).

Example 4

Detection of Anti-PAD3 Autoantibodies in Serum of Rheumatoid Arthritis Subjects

This example demonstrates that the anti-PAD3 autoantibody assay provided in this disclosure can be used to detect anti-PAD3 auto-antibodies in the serum of subjects with rheumatoid arthritis. Serum samples collected at baseline (at time of study entry) of subjects in three independent clinical trials of mavrilimumab were tested using the anti-PAD3 autoantibody assay of Example 3. TABLE 2 shows the results of anti-PAD3 autoantibody detection in all subjects tested from each of the three clinical trials. In all three of these studies, a minority of tested subjects had detectable anti-PAD3 autoantibodies (defined as above the LLOQ for the assay, a ratio of detected ECL counts in the tested serum sample: ECL counts in a negative control sample ≥1.37), with 16% (Study A), 24% (Study B) and 31% (Study C) of subjects testing positive as shown below in TABLE 2.

TABLE 2

Anti-PAD3 Autoantibody Detection in RA Subject Serum

| Study | Status | n | Percent |
|---|---|---|---|
| A | Anti-PAD3+ | 51 | 16 |
|   | Anti-PAD3− | 272 | 84 |
| B | Anti-PAD3+ | 69 | 25 |
|   | Anti-PAD3− | 211 | 75 |
| C | Anti-PAD3+ | 42 | 31 |
|   | Anti-PAD3− | 94 | 69 |

Example 5

A Phase 2b, Randomized, Double-Blind Study to Evaluate the Efficacy and Safety of Mavrilimumab in Subjects with Moderate-to-Severe Rheumatoid Arthritis Study A was a Phase 2b, randomized, double-blind, placebo-controlled, parallel group, multicenter study evaluating the efficacy and safety of 3 subcutaneous (SC) doses of mavrilimumab in combination with methotrexate (MTX) in subjects 18-80 years of age with adult onset RA (defined by the 2010 American College of Rheumatology [ACR] and European League Against Rheumatism [EULAR] classification criteria), with inadequate response to one or more conventional disease-modifying anti-rheumatic drugs (DMARDs), and at least moderately active disease (defined by Disease Activity Score in 28 joints [DAS28]≥3.2C-reactive protein [CRP]/erythrocyte sedimentation rate [ESR]) and at least 4 swollen joints despite treatment with MTX.

The key inclusion criteria were
- A diagnosis of adult onset RA defined by the 2010 ACR/EULAR classification criteria (Aletaha et al, 2010)
- At least moderately active disease as defined by DAS28 (CRP) ≥3.2 at screening and DAS28(ESR) ≥3.2 at Day 1 (van Gestel et al, 1998)
- At least 4 swollen joints at screening and Day 1
- Subjects with inadequate response to one or more conventional DMARDs
- Receiving oral or injectable MTX (7.5-25.0 mg/week) for 12 weeks prior to screening with at least the last 4 weeks prior to screening at a stable dose A total of 326 subjects were randomized in a 1:1:1:1 ratio to receive one of 3 SC doses of mavrilimumab (30, 100, or 150 mg) or placebo Q2W for 24 weeks along with a stable dose of oral or injectable MTX (7.5 25.0 mg/week) as follows:
- Treatment Arm 1: 30 mg SC mavrilimumab Q2W+MTX (n=70)
- Treatment Arm 2: 100 mg SC mavrilimumab Q2W+MTX (n=70)
- Treatment Arm 3: 150 mg SC mavrilimumab Q2W+MTX (n=70)
- Treatment Arm 4: SC placebo Q2W+MTX (n=70)

Subjects received investigational product (mavrilimumab or placebo) by SC injection starting on Week 0 (Day 1) and continued to receive investigational product Q2W for 24 weeks. The primary analysis of the study was conducted once the last subject in the study completed the Week 24 visit. The co-primary endpoints of the study were the change from Day 1 DAS28(CRP) score at Week 12 (Day 85) and ACR 20% improvement criteria (ACR20) at Week 24 (Day 169). The change from baseline DAS28(CRP) at Week 12 (Day 85) was analyzed using a repeated measures model, adjusting for Day 1 DAS28(CRP). Efficacy was evaluated by ACR20, ACR 50% improvement criteria (ACR50), and ACR 70% improvement criteria (ACR70) response rates at each visit using logistic regression.

Subgroup Analysis: Baseline Anti-PAD4 Autoantibodies

To explore the relationship between clinical response to mavrilimumab and peripheral blood biomarkers associated with neutrophil and macrophage biology, subgroups defined by baseline positivity or negativity for detectable anti-PAD4 autoantibodies were analyzed. Positivity for anti-PAD4 autoantibodies was defined as having measured levels of anti-PAD4 autoantibodies above the LLOQ for the assay. Baseline serum samples were available from 323 of the 326 subjects in the study and were tested for anti-PAD4 autoantibodies. Overall, 32% of the subjects tested positive for anti-PAD4 autoantibodies, with similar percentages positive in each of the treatment arms as depicted below, on TABLE 3.

TABLE 3

Summary of Anti-PAD4 Autoantibody Analysis

| Treatment arm | Anti-PAD4 positive | Anti-PAD4 negative |
|---|---|---|
| Placebo | 32% | 68% |
| Mavrilimumab 30 mg | 34% | 66% |
| Mavrilimumab 100 mg | 29% | 71% |
| Mavrilimumab 150 mg | 34% | 66% |

A subgroup analysis was performed for each of the clinical endpoints, including ACR20, ACR50, ACR70 and DAS28(CRP) at the time of the primary endpoint, after 24 weeks of treatment. Across these clinical endpoints, a significant treatment*biomarker interaction was observed. For the ACR20 endpoint, there was a significant treatment*biomarker interaction (p=0.045) such that the anti-PAD4 negative subgroup demonstrated a much better response to mavrilimumab compared to placebo, whereas the anti-PAD4 positive subgroup demonstrated a small difference in response to mavrilimumab relative to placebo across dose groups (see results below in TABLE 4). For example, the ACR20 response in the 150 mg mavrilimumab treatment arm in the anti-PAD4 negative subgroup was 77% (Δ compared to placebo=60%), while in the anti-PAD4 positive subgroup, the ACR20 response was 67% (Δ compared to placebo=27%).

TABLE 4

ACR20 responses (%) in anti-PAD4 autoantibody positive and negative subgroups at Week 24

| Treatment Arm | Overall | Overall (Δ Pbo) | Anti-PAD4 Neg | Anti-PAD4 Neg (Δ Pbo) | Anti-PAD4 Pos | Anti-PAD4 Pos (Δ Pbo) |
|---|---|---|---|---|---|---|
| Placebo | 25 | 0 | 17 | 6 | 40 | 0 |
| Mavrilimumab 30 mg | 51 | 26 | 45 | 29 | 59 | 19 |
| Mavrilimumab 100 mg | 61 | 36 | 65 | 48 | 52 | 12 |
| Mavrilimumab 150 mg | 73 | 49 | 77 | 60 | 67 | 27 |

A similar effect was observed for the ACR50 response and again there was a significant treatment*biomarker interaction (p=0.024). For example, the ACR50 response in the 150 mg mavrilimumab treatment arm in the anti-PAD4 negative subgroup was 40% (Δ compared to placebo=37%), while in the anti-PAD4 positive subgroup, the ACR50 response was 41% (Δ compared to placebo=9%; see TABLE 56, below).

TABLE 5

ACR50 responses (%) in anti-PAD4 autoantibody positive and negative subgroups at Week 24

| Treatment Arm | Overall | Overall (Δ Pbo) | Anti-PAD4 Neg | Anti-PAD4 Neg (Δ Pbo) | Anti-PAD4 Pos | Anti-PAD4 Pos (Δ Pbo) |
|---|---|---|---|---|---|---|
| Placebo | 12 | 0 | 4 | 0 | 32 | 0 |
| Mavrilimumab 30 mg | 28 | 16 | 23 | 19 | 37 | 5 |
| Mavrilimumab 100 mg | 26 | 14 | 28 | 25 | 20 | −12 |
| Mavrilimumab 150 mg | 41 | 28 | 40 | 37 | 41 | 9 |

A similar effect was observed for the ACR70 response. For example, the ACR70 response in the 150 mg mavrilimumab treatment arm in the anti-PAD4 negative subgroup was 15% (Δ compared to placebo=15%), while in the anti-PAD4 positive subgroup, the ACR70 response was 11% (Δ compared to placebo=−1%; TABLE 6). Therefore, the difference in response to mavrilimumab relative to placebo was consistent across ACR20, ACR50 and ACR70 endpoints. In addition, the difference in response rates in the mavrilimumab treatment groups relative to placebo increased in magnitude in the clinical response measures of greater magnitude (i.e. ACR50 and ACR70).

TABLE 6

ACR70 responses (%) in anti-PAD4 autoantibody positive and negative subgroups at Week 24

| Treatment Arm | Overall | Overall (Δ Pbo) | Anti-PAD4 Neg | Anti-PAD4 Neg (Δ Pbo) | Anti-PAD4 Pos | Anti-PAD4 Pos (Δ Pbo) |
|---|---|---|---|---|---|---|
| Placebo | 4 | 0 | 0 | 0 | 12 | 0 |
| Mavrilimumab 30 mg | 12 | 9 | 11 | 11 | 15 | 3 |
| Mavrilimumab 100 mg | 11 | 7 | 10 | 10 | 12 | 0 |
| Mavrilimumab 150 mg | 14 | 10 | 15 | 15 | 11 | −1 |

The effect of this biomarker was also tested using a fourth measure of clinical response, the change in DAS28(CRP). A significant treatment*biomarker interaction (p=0.002) was observed for baseline anti-PAD4 autoantibody levels with the DAS28(CRP) endpoint. For example, the change in DAS28(CRP) in the 150 mg mavrilimumab treatment arm in the anti-PAD4 negative subgroup was −2.15 (Δ compared to placebo=−1.44), while in the anti-PAD4 positive subgroup, the change in DAS28(CRP) was −2.24 (Δ compared to placebo=−0.71). See TABLE 7, below.

TABLE 7

Change in DAS28(CRP) in anti-PAD4 autoantibody positive and negative subgroups at Week 24

| Treatment Arm | Overall | Overall (Δ Pbo) | Anti-PAD4 Neg | Anti-PAD4 Neg (Δ Pbo) | Anti-PAD4 Pos | Anti-PAD4 Pos (Δ Pbo) |
|---|---|---|---|---|---|---|
| Placebo | −0.96 | 0 | −0.71 | 0 | −1.53 | 0 |
| Mavrilimumab 30 mg | −1.74 | −0.78 | −1.62 | −0.91 | −1.96 | −0.43 |
| Mavrilimumab 100 mg | −1.98 | −1.02 | −2.14 | −1.43 | −1.61 | −0.08 |
| Mavrilimumab 150 mg | −2.18 | −1.22 | −2.15 | −1.44 | −2.24 | −0.71 |

Similar trends as those seen with study A were seen with study B.

Subgroup Analysis: Baseline Anti-PAD3 Autoantibodies

To explore the relationship between clinical response to mavrilimumab and autoantibodies to PAD3, a second protein in the protein-arginine deiminase family, subgroups defined by baseline positivity or negativity for detectable anti-PAD3 autoantibodies were analyzed. Positivity for anti-PAD3 autoantibodies was defined as having measured levels of anti-PAD3 autoantibodies above the LLOQ for the assay. Baseline serum samples were available from 323 of the 326 subjects in the study and were tested for anti-PAD3 autoantibodies. As seen in TABLE 8, below, overall, 16% of the subjects tested positive for anti-PAD3 autoantibodies, with similar percentages positive in each of the treatment arms.

TABLE 8

Summary of Anti-PAD3 Autoantibody Analysis

| Treatment arm | Anti-PAD3 positive | Anti-PAD3 negative |
|---|---|---|
| Placebo | 16% | 84% |
| Mavrilimumab 30 mg | 11% | 89% |
| Mavrilimumab 100 mg | 21% | 79% |
| Mavrilimumab 150 mg | 14% | 86% |

A subgroup analysis was performed for each of the clinical endpoints, including ACR20, ACR50, ACR70 and DAS28(CRP) at the time of the primary endpoint, after 24 weeks of treatment. Across these clinical endpoints, no significant treatment*biomarker interaction was observed. As shown in TABLE 9, below, for the ACR20 endpoint, there was no significant treatment*biomarker interaction such that the anti-PAD3 positive and negative subgroups demonstrated a similar response to mavrilimumab compared to placebo. For example, the ACR20 response in the 150 mg mavrilimumab treatment arm in the anti-PAD3 negative subgroup was 74% (Δ compared to placebo=50%), while in the anti-PAD3 positive subgroup, the ACR20 response was 73% (Δ compared to placebo=50%).

TABLE 9

ACR20 responses (%) in anti-PAD3 autoantibody positive and negative subgroups at Week 24

| Treatment Arm | Overall | Overall (Δ Pbo) | Anti-PAD3 Neg | Anti-PAD3 Neg (Δ Pbo) | Anti-PAD3 Pos | Anti-PAD3 Pos (Δ Pbo) |
|---|---|---|---|---|---|---|
| Placebo | 25 | 0 | 24 | 0 | 23 | 0 |
| Mavrilimumab 30 mg | 51 | 26 | 48 | 24 | 67 | 44 |
| Mavrilimumab 100 mg | 61 | 36 | 63 | 39 | 56 | 33 |
| Mavrilimumab 150 mg | 73 | 49 | 74 | 50 | 73 | 50 |

As shown below in TABLE 10, similar effect was observed for the ACR50 response and again there was no significant treatment*biomarker interaction. For example, the ACR50 response in the 150 mg mavrilimumab treatment arm in the anti-PAD3 negative subgroup was 40% (Δ compared to placebo=28%), while in the anti-PAD3 positive subgroup, the ACR50 response was 45% (Δ compared to placebo=30%).

TABLE 10

ACR50 responses (%) in anti-PAD3 autoantibody positive and negative subgroups at Week 24

| Treatment Arm | Overall | Overall (Δ Pbo) | Anti-PAD3 Neg | Anti-PAD3 Neg (Δ Pbo) | Anti-PAD3 Pos | Anti-PAD3 Pos (Δ Pbo) |
|---|---|---|---|---|---|---|
| Placebo | 12 | 0 | 12 | 0 | 15 | 0 |
| Mavrilimumab 30 mg | 28 | 16 | 27 | 15 | 33 | 18 |
| Mavrilimumab 100 mg | 26 | 14 | 28 | 16 | 17 | 2 |
| Mavrilimumab 150 mg | 41 | 28 | 40 | 28 | 45 | 30 |

As shown below, in TABLE 11, a similar effect was observed for the ACR70 response. For example, the ACR70 response in the 150 mg mavrilimumab treatment arm in the anti-PAD3 negative subgroup was 15% (Δ compared to placebo=10%), while in the anti-PAD3 positive subgroup, the ACR70 response was 9% (Δ compared to placebo=9%). Therefore, the difference in response to mavrilimumab relative to placebo was consistent across ACR20, ACR50 and ACR70 endpoints. In addition, the difference in response rates in the mavrilimumab treatment groups relative to placebo did not change in magnitude in the clinical response measures of greater magnitude (i.e. ACR50 and ACR70).

TABLE 11

ACR70 responses (%) in anti-PAD3 autoantibody positive and negative subgroups at Week 24

| Treatment Arm | Overall | Overall (Δ Pbo) | Anti-PAD3 Neg | Anti-PAD3 Neg (Δ Pbo) | Anti-PAD3 Pos | Anti-PAD3 Pos (Δ Pbo) |
|---|---|---|---|---|---|---|
| Placebo | 4 | 0 | 5 | 0 | 0 | 0 |
| Mavrilimumab 30 mg | 12 | 9 | 13 | 8 | 11 | 11 |
| Mavrilimumab 100 mg | 11 | 7 | 9 | 4 | 17 | 17 |
| Mavrilimumab 150 mg | 14 | 10 | 15 | 10 | 9 | 9 |

The effect of this biomarker was also tested using a fourth measure of clinical response, the change in DAS28(CRP). As shown below in TABLE 12, no significant treatment*biomarker interaction was observed for baseline anti-PAD3 autoantibody levels with the DAS28(CRP) endpoint. For example, the change in DAS28(CRP) in the 150 mg mavrilimumab treatment arm in the anti-PAD3 negative subgroup was −2.13 (Δ compared to placebo=−1.15), while in the anti-PAD3 positive subgroup, the change in DAS28 (CRP) was −2.47 (Δ compared to placebo=−1.73). These results indicate that the treatment*biomarker interaction obtained for anti-PAD4 antibodies is specific for anti-PAD4 antibody reactivity and is not a general effect that extends to all members of the protein-arginine deiminase family.

TABLE 12

Change in DAS28(CRP) in anti-PAD3 autoantibody positive and negative subgroups at Week 24

| Treatment Arm | Overall | Overall (Δ Pbo) | Anti-PAD3 Neg | Anti-PAD3 Neg (Δ Pbo) | Anti-PAD3 Pos | Anti-PAD3 Pos (Δ Pbo) |
|---|---|---|---|---|---|---|
| Placebo | −0.96 | 0 | −0.98 | 0 | −0.74 | 0 |
| Mavrilimumab 30 mg | −1.74 | −0.78 | −1.67 | −0.69 | −2.13 | −1.39 |
| Mavrilimumab 100 mg | −1.98 | −1.02 | −2.07 | −1.09 | −1.62 | −0.88 |
| Mavrilimumab 150 mg | −2.18 | −1.22 | −2.13 | −1.15 | −2.47 | −1.73 |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

TABLE 13

Amino Acid Sequences.

| SEQ ID NO | Sequence | Description |
|---|---|---|
| 1 | MLLLVTSLLLCELPHPAFLLIPEKSDLRT VAPASSLNVRFDSRTMNLSWDCQENTTFS KCFLTDKKNRVVEPRLSNNECSCTFREIC LHEGVTFEVHVNTSQRGFQQKLLYPNSGR EGTAAQNFSCFIYNADLMNCTWARGPTAP RDVQYFLYIRNSKRRREIRCPYYIQDSGT HVGCHLDNLSGLTSRNYFLVNGTSREIGI QFFDSLLDTKKIERFNPPSNVTVRCNTTH CLVRWKQPRTYQKLSYLDFQYQLDVHRKN TQPGTENLLINVSGDLENRYNFPSSEPRA KHSVKIRAADVRILNWSSWSEAIEFGSDD GNLGSVYIYVLLIVGTLVCGIVLGFLFKR FLRIQRLFPPVPQIKDKLNDNHEVEDEII WEEFTPEEGKGYREEVLTVKEIT | Granulocyte-macrophage colony-stimulating factor receptor subunit alpha (GM-CSFRα) Uniprot: P15509\|CSF2R_HUMAN |
| 2 | QVQLVQSGAEVKKPGASVKVSCKVSGYTL TELSIHWVRQAPGKGLEWMGGFDPEENEI VYAQRFQGRVTMTEDTSTDTAYMELSSLR SEDTAVYYCAIVGSFSPLTLGLWGQGTMV TVSSASTKGPSVFPLAPCSRSTSESTAAL GCLVKDYFPEPVTVSWNSGALTSGVHTFP AVLQSSGLYSLSSVVTVPSSSLGTKTYTC NVDHKPSNTKVDKRVESKYGPPCPSCPAP EFLGGPSVFLFPPKPKDTLMISRTPEVTC VVVDVSQEDPEVQFNWYVDGVEVHNAKTK PREEQFNSTYRVVSVLTVLHQDWLNGKEY KCKVSNKGLPSSIEKTISKAKGQPREPQV YTLPPSQEEMTKNQVSLTCLVKGFYPSDI AVEWESNGQPENNYKTTPPVLDSDGSFFL YSRLTVDKSRWQEGNVFSCSVMHEALHNH YTQKSLSLSLGK | Mavrilimumab heavy chain (HC) |
| 3 | QSVLTQPPSVSGAPGQRVTISCTGSGSNI GAPYDVSWYQQLPGTAPKLLIYHNNKRPS GVDRFSGSKSGTSASLAITGLQAEDEADY YCATVEAGLSGSVFGGGTKLTVLGQPKAA PSVTLFPPSSEELQANKATLVCLISDFYP GAVTVAWKADSSPVKAGVETTTPSKQSNN KYAASSYLSLTPEQWKSHRSYSCQVTHEG STVEKTVAPTECS | Mavrilimumab light chain (LC) |
| 4 | QVQLVQSGAEVKKPGASVKVSCKVSGYTL TELSIHWVRQAPGKGLEWMGGFDPEENEI VYAQRFQGRVTMTEDTSTDTAYMELSSLR SEDTAVYYCAIVGSFSPLTLGLWGQGTMV TVS | Mavrilimumab heavy chain variable region (VH) |
| 5 | QSVLTQPPSVSGAPGQRVTISCTGSGSNI GAPYDVSWYQQLPGTAPKLLIYHNNKRPS GVPDRFSGSKSGTSASLAITGLQAEDEAD YYCATVEAGLSGSVFGGGTKLTVL | Mavrilimumab light chain variable region (VL) |
| 6 | YTLTELSIH | Mavrilimumab VH-CDR1 (VH 27-35) |

TABLE 13-continued

Amino Acid Sequences.

| SEQ ID NO | Sequence | Description |
|---|---|---|
| 7 | WMGGFDPEENEIVY | Mavrilimumab VH-CDR2 (VH 47-60) |
| 8 | IVGSFSPLTLGL | Mavrilimumab VH-CDR3 (VH 98-109) |
| 9 | GSNIGAPYDVS | Mavrilimumab VL-CDR1 (VL 26-36) |
| 10 | LLIYHNNKRPS | Mavrilimumab VL-CDR2 (VL 48-58) |
| 11 | ATVEAGLSGS | Mavrilimumab VL-CDR3 (VL 91-100) |
| 12 | YLDFQ | Mavrilimumab epitope (GM-CSFα 226-230) |
| 13 | MAQGTLIRVTPEQPTHAVCVLGTLTQLDICSSAPEDCTSFSINASPGVVVDIAHGPPAKKKSTGSSTWPLDPGVEVTLTMKVASGSTGDQKVQISYYGPKTPPVKALLYLTGVEISLCADITRTGKVKPTRAVKDQRTWTWGPCGQGAILLVNCDRDNLESSAMDCEDDEVLDSEDLQDMSLMTLSTKTPKDFFTNHTLVLHVARSEMDKVRVFQATRGKLSSKCSVVLGPKWPSHYLMVPGGKHNMDFYVEALAFPDTDFPGLITLTISLLDTSNLELPEAVVFQDSVVFRVAPWIMTPNTQPPQEVYACSIFENEDFLKSVTTLAMKAKCKLTICPEEENMDDQWMQDEMEIGYIQAPHKTLPVVFDSPRNRGLKEFPIKRVMGPDFGYVTRGPQTGGISGLDSFGNLEVSPPVTVRGKEYPLGRILFGDSCYPSNDSRQMHQALQDFLSAQQVQAPVKLYSDWLSVGHVDEFLSFVPAPDRKGFRLLLASPRSCYKLFQEQQNEGHGEALLFEGIKKKKQQKIKNILSNKTLREHNSFVERCIDWNRELLKRELGLAESDIIDIPQLFKLKEFSKAEAFFPNMVNMLVLGKHLGIPKPFGPVINGRCCLEEKVCSLLEPLGLQCTFINDFFTYHIRHGEVHCGTNVRRKPFSFKWWNMVP | Protein-arginine deiminase type-4 (PAD4) Uniprot: Q9UM07\|PADI4_HUMAN |

---

What is claimed is:

1. A method of treating a rheumatoid arthritis patient comprising
   identifying the rheumatoid arthritis patient having anti-peptidylarginine deiminase 4 (anti-PAD4) autoantibody level below the lower limit of quantification (LLOQ) for an assay; and
   administering an antibody or antigen-binding fragment thereof that specifically binds to human granulocyte macrophage colony-stimulating factor receptor alpha (GM-CSFRa) to the patient;
   wherein the antibody or antigen-binding fragment thereof comprises complementary determining regions having the amino acid sequence set forth in SEQ ID NOs: 6 to 11; and
   wherein the LLOQ for the assay is 5000 U/ml.

2. The method of claim 1, wherein the antibody or antigen-binding fragment thereof that specifically binds to GM-CSFRα comprises a heavy chain variable region having the amino acid sequence set forth in SEQ ID NO: 4 and/or a light chain variable region having the amino acid sequence set forth in SEQ ID NO: 5.

3. The method of claim 1, wherein the patient has been treated with one or more additional Disease-modifying antirheumatic drugs (DMARDs), either before, during, or after administration of an antibody or antigen-binding fragment thereof that specifically binds to GM-CSFRα.

4. The method claim 1, wherein the anti-PAD4 autoantibody level is detected in one or more of the patient's whole blood, blood serum, plasma, or synovial fluid.

5. The method according to claim 4, wherein the anti-PAD4 autoantibody level is detected in the patient's blood serum.

6. The method of claim 1, further comprising a step of determining, submitting a sample taken from the patient for determination, or instructing a clinical laboratory to determine the expression level or activity of one or more additional biomarkers, or to determine at least one clinical status marker, or a combination thereof.

7. The method of claim 1, wherein the antibody or antigen-binding fragment thereof that specifically binds to GM-CSFRa is administered at a fixed dose.

8. The method of claim 1, wherein the assay is an immunoassay, an agglutination assay, or a homogeneous assay.

9. The method according to claim 8, wherein the assay is an immunoassay, and the immunoassay employs detectably labeled PAD4.

10. The method according to claim 9, wherein the detectably labeled PAD4 is ruthenylated PAD4.

11. The method of claim 8, wherein the immunoassay detects anti-PAD4-autoantibody bound to PAD4.

* * * * *

SEQUENCE LISTING

<160> NUMBER OF SEQ ID NOS: 14

<210> SEQ ID NO 1
<211> LENGTH: 400
<212> TYPE: PRT
<213> ORGANISM: Homo sapiens

<400> SEQUENCE: 1

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
            195                 200                 205

Leu Leu Asp Thr Lys Lys Ile Glu Arg Phe Asn Pro Pro Ser Asn Val
            210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
            245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
            275                 280                 285

Arg Ala Lys His Ser Val Lys Ile Arg Ala Ala Asp Val Arg Ile Leu
            290                 295                 300

Asn Trp Ser Ser Trp Ser Glu Ala Ile Glu Phe Gly Ser Asp Asp Gly
305                 310                 315                 320

Asn Leu Gly Ser Val Tyr Ile Tyr Val Leu Leu Ile Val Gly Thr Leu
            325                 330                 335

Val Cys Gly Ile Val Leu Gly Phe Leu Phe Lys Arg Phe Leu Arg Ile
            340                 345                 350

Gln Arg Leu Phe Pro Pro Val Pro Gln Ile Lys Asp Lys Leu Asn Asp
            355                 360                 365

Asn His Glu Val Glu Asp Glu Ile Ile Trp Glu Phe Thr Pro Glu
            370                 375                 380

Glu Gly Lys Gly Tyr Arg Glu Glu Val Leu Thr Val Lys Glu Ile Thr
385                 390                 395                 400

<210> SEQ ID NO 2
<211> LENGTH: 447
<212> TYPE: PRT
<213> ORGANISM: Artificial Sequence
<220> FEATURE:
<223> OTHER INFORMATION: Synthetic polypeptide

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
            35                  40                  45

Gly Gly Phe Asp Pro Glu Glu Asn Glu Ile Val Tyr Ala Gln Arg Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ile Val Gly Ser Phe Ser Pro Leu Thr Leu Gly Leu Trp Gly Gln
            100                 105                 110

Gly Thr Met Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 3
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 3

Gln Ser Val Leu Thr Gln Pro Pro Ser Val Ser Gly Ala Pro Gly Gln
1               5                   10                  15

Arg Val Thr Ile Ser Cys Thr Gly Ser Gly Ser Asn Ile Gly Ala Pro
            20                  25                  30

Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Asp Arg Phe Ser
    50                  55                  60

```
Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Ala Thr Val Glu Ala Gly Leu
                 85                  90                  95

Ser Gly Ser Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 4
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Glu Asn Glu Ile Val Tyr Ala Gln Arg Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Ile Val Gly Ser Phe Ser Pro Leu Thr Leu Gly Leu Trp Gly Gln
            100                 105                 110

Gly Thr Met Val Thr Val Ser
        115

<210> SEQ ID NO 5
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 5

Gln Ser Val Leu Thr Gln Pro Pro Ser Val Ser Gly Ala Pro Gly Gln
1               5                   10                  15

Arg Val Thr Ile Ser Cys Thr Gly Ser Gly Ser Asn Ile Gly Ala Pro
            20                  25                  30
```

```
Tyr Asp Val Ser Trp Tyr Gln Gln Leu Pro Gly Thr Ala Pro Lys Leu
        35                  40                  45

Leu Ile Tyr His Asn Asn Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ala Thr Val Glu Ala Gly
                85                  90                  95

Leu Ser Gly Ser Val Phe Gly Gly Gly Thr Lys Leu Thr Val Leu
            100                 105                 110

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Tyr Thr Leu Thr Glu Leu Ser Ile His
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 7

Trp Met Gly Gly Phe Asp Pro Glu Glu Asn Glu Ile Val Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 8

Ile Val Gly Ser Phe Ser Pro Leu Thr Leu Gly Leu
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

Gly Ser Asn Ile Gly Ala Pro Tyr Asp Val Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 10

Leu Leu Ile Tyr His Asn Asn Lys Arg Pro Ser
```

-continued

```
<210> SEQ ID NO 11
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 11

Ala Thr Val Glu Ala Gly Leu Ser Gly Ser
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 12

Tyr Leu Asp Phe Gln
1               5

<210> SEQ ID NO 13
<211> LENGTH: 663
<212> TYPE: PRT
<213> ORGANISM: Homo sapiens

<400> SEQUENCE: 13

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
```

```
                225                 230                 235                 240
Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
                260                 265                 270

Asp Thr Ser Asn Leu Glu Leu Pro Glu Ala Val Val Phe Gln Asp Ser
                275                 280                 285

Val Val Phe Arg Val Ala Pro Trp Ile Met Thr Pro Asn Thr Gln Pro
                290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
                340                 345                 350

Glu Ile Gly Tyr Ile Gln Ala Pro His Lys Thr Leu Pro Val Val Phe
                355                 360                 365

Asp Ser Pro Arg Asn Arg Gly Leu Lys Glu Phe Pro Ile Lys Arg Val
                370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
                420                 425                 430

Ser Cys Tyr Pro Ser Asn Asp Ser Arg Gln Met His Gln Ala Leu Gln
                435                 440                 445

Asp Phe Leu Ser Ala Gln Gln Val Gln Ala Pro Val Lys Leu Tyr Ser
                450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Gln Asn Glu Gly His Gly Glu Ala
                500                 505                 510

Leu Leu Phe Glu Gly Ile Lys Lys Lys Gln Gln Lys Ile Lys Asn
                515                 520                 525

Ile Leu Ser Asn Lys Thr Leu Arg Glu His Asn Ser Phe Val Glu Arg
                530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
                580                 585                 590

Gly Lys His Leu Gly Ile Pro Lys Pro Phe Gly Pro Val Ile Asn Gly
                595                 600                 605

Arg Cys Cys Leu Glu Glu Lys Val Cys Ser Leu Leu Glu Pro Leu Gly
                610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655
```

```
Lys Trp Trp Asn Met Val Pro
            660

<210> SEQ ID NO 14
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 14

His His His His His His His His His His
1               5                   10
```